US009017725B2

(12) United States Patent
Mitra et al.

(10) Patent No.: US 9,017,725 B2
(45) Date of Patent: *Apr. 28, 2015

(54) TOPICAL DRUG DELIVERY SYSTEMS FOR OPHTHALMIC USE

(75) Inventors: Ashim K. Mitra, Overland Park, KS (US); Poonam R. Velagaleti, Randolph, NJ (US); Ulrich M. Grau, New York, NY (US)

(73) Assignee: Aurinia Pharmaceuticals Inc., Victoria, BC (CA)

( * ) Notice: Subject to any disclaimer, the term of this patent is extended or adjusted under 35 U.S.C. 154(b) by 403 days.

This patent is subject to a terminal disclaimer.

(21) Appl. No.: 12/774,600

(22) Filed: May 5, 2010

(65) Prior Publication Data

US 2010/0310642 A1    Dec. 9, 2010

Related U.S. Application Data

(60) Provisional application No. 61/185,396, filed on Jun. 9, 2009.

(51) Int. Cl.
| A61K 9/14 | (2006.01) |
| A61K 31/56 | (2006.01) |
| A61K 31/573 | (2006.01) |
| A61K 9/00 | (2006.01) |
| A61K 9/107 | (2006.01) |
| A61K 31/14 | (2006.01) |
| A61K 31/436 | (2006.01) |
| A61K 47/10 | (2006.01) |
| A61K 47/22 | (2006.01) |

(52) U.S. Cl.
CPC ............ *A61K 31/573* (2013.01); *A61K 9/0048* (2013.01); *A61K 9/107* (2013.01); *A61K 31/14* (2013.01); *A61K 31/436* (2013.01); *A61K 47/10* (2013.01); *A61K 47/22* (2013.01); *Y10S 514/912* (2013.01)

(58) Field of Classification Search
USPC ...................................................... 424/489
See application file for complete search history.

(56) References Cited

U.S. PATENT DOCUMENTS

| 3,244,592 A | 4/1966 | Tadashi |
| 4,039,662 A | 8/1977 | Hecht |
| 4,117,118 A | 9/1978 | Harri |
| 4,120,949 A | 10/1978 | Bapatla |
| 4,409,205 A | 10/1983 | Shively |
| 4,649,047 A | 3/1987 | Kaswan |
| 4,744,980 A | 5/1988 | Holly |
| 4,795,643 A | 1/1989 | Seth |
| 4,804,539 A | 2/1989 | Guo |
| 4,839,342 A | 6/1989 | Kaswan |
| 4,865,846 A | 9/1989 | Kaufman |
| 4,883,658 A | 11/1989 | Holly |
| 5,051,402 A | 9/1991 | Kurihara |
| 5,075,104 A | 12/1991 | Gressel |
| 5,110,493 A | 5/1992 | Cherng-Chyi |
| 5,188,826 A | 2/1993 | Chandrasekaran |
| 5,209,927 A | 5/1993 | Gressel |
| 5,227,372 A | 7/1993 | Folkman |
| 5,252,246 A | 10/1993 | Ding |
| 5,252,318 A | 10/1993 | Joshi |
| 5,326,761 A | 7/1994 | Rozier |
| 5,342,625 A | 8/1994 | Hauer |
| 5,360,611 A | 11/1994 | Robertson |
| 5,387,589 A | 2/1995 | Kulkarni |
| 5,401,510 A | 3/1995 | Robertson |
| 5,411,952 A | 5/1995 | Kaswan |
| 5,414,011 A | 5/1995 | Fu et al. |
| 5,441,732 A | 8/1995 | Hoeg |
| 5,474,979 A | 12/1995 | Ding |
| 5,496,861 A | 3/1996 | Rouse, 3 et al. |
| 5,540,931 A | 7/1996 | Hewitt |
| 5,558,876 A | 9/1996 | Desai |
| 5,576,025 A | 11/1996 | Akiyama et al. |
| 5,585,406 A | 12/1996 | Ding |
| 5,591,426 A | 1/1997 | Dabrowski |
| 5,599,534 A | 2/1997 | Himmelstein |

(Continued)

FOREIGN PATENT DOCUMENTS

| EP | 0349061 | 3/1995 |
| EP | 0 868 909 | 10/1998 |

(Continued)

OTHER PUBLICATIONS

Winfield, Pharmaceutical Practice, Ophthalmic Products—pH adjustment, Churchill Livingstone, 2004, 264-269.*
University Federico II of Naples , Italy and European Chemistry Thematic Network, Polar heads and tails, Oct. 15, 2007, printed from http://www.whatischemistry.unina.it/en/amphi.html, Google date sheet included, 3 pages.*
Anglade E. et al., Next-Generation Calcineurin Inhibitors for Ophthalmic Indications, *Expert Opin. Investig. Drugs*, vol. 16, No. 10, pp. 1525-1540 (Oct. 2007).
Benitez del Castillo et al. Influence of Topically Applied Cyclosporine A in Olive Oil on Corneal Epithelium Permeability. Cornea vol. 13(2):136-40, (Mar. 1994).
Blanco-Fuente et al. Tanned Leather: A Good Model for Determining Hydrogels Bioadhesion. International Journal of Pharmaceutics, vol. 138(1):103-112, (Jul. 12, 1996).
Bonduelle et al. Tissue Concentration of Nanoencapsulated Radio-Labelled Cyclosporin Following Peroral Delivery in Mice or Ophthalmic Application in Rabbits. European Journal of Pharmacology and Biopharmacology, vol. 42(5):313-319, (Oct. 19, 1996).
Booth, B. et al., Sustained-Release Ophthalmic Drug Delivery Systems for Treatment of Macular Disorders, *Drugs & Aging*, vol. 24, No. 7, pp. 581-602 (Jul. 2007).
Chang et al. The Effect of Water-Soluble Vitamin E on Cyclosporine Pharmacokinetics in Healthy Volunteers. Clinical Pharmacology & Therapeutics, 59(3):297-303, (Mar. 1996).

(Continued)

*Primary Examiner* — Gigi Huang
(74) *Attorney, Agent, or Firm* — Greenberg Traurig, LLP; David J. Dykeman; Fang Xie

(57) ABSTRACT

Topical drug delivery systems for ophthalmic use including mixed nanomicellar formulations of water-insoluble drugs and methods of treating diseases affecting the posterior ocular segments are disclosed. In an embodiment, an aqueous ophthalmic solution includes nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v.

16 Claims, 1 Drawing Sheet

(56) References Cited

U.S. PATENT DOCUMENTS

| | | | |
|---|---|---|---|
| 5,607,698 A | 3/1997 | Martin | |
| 5,624,893 A | 4/1997 | Yanni | |
| 5,643,870 A | 7/1997 | Boelsterli | |
| 5,698,219 A | 12/1997 | Valdivia | |
| 5,698,533 A | 12/1997 | Kang | |
| 5,741,512 A | 4/1998 | Hauer | |
| 5,770,628 A | 6/1998 | Cantoro | |
| 5,773,019 A | 6/1998 | Ashton | |
| 5,798,333 A | 8/1998 | Sherman | |
| 5,814,655 A | 9/1998 | Patel | |
| 5,830,508 A | 11/1998 | MacKeen | |
| 5,843,891 A | 12/1998 | Sherman | |
| 5,866,159 A | 2/1999 | Hauer | |
| 5,869,103 A | 2/1999 | Yeh | |
| 5,886,030 A | 3/1999 | Maniar | |
| 5,916,589 A | 6/1999 | Hauer | |
| 5,962,014 A | 10/1999 | Hauer | |
| 5,962,017 A | 10/1999 | Hauer | |
| 5,998,365 A | 12/1999 | Sherman | |
| 6,007,840 A | 12/1999 | Hauer | |
| 6,024,978 A | 2/2000 | Hauer | |
| 6,071,958 A | 6/2000 | Jimenez-Bayardo | |
| 6,165,500 A | 12/2000 | Cevc | |
| 6,193,985 B1 | 2/2001 | Sonne | |
| 6,217,895 B1 * | 4/2001 | Guo et al. | 424/427 |
| 6,254,860 B1 | 7/2001 | Garst | |
| 6,254,893 B1 | 7/2001 | MacKeen | |
| 6,284,235 B1 | 9/2001 | Foreman et al. | |
| 6,309,569 B1 | 10/2001 | Farrar | |
| 6,309,630 B1 | 10/2001 | Patel | |
| 6,350,442 B2 | 2/2002 | Garst | |
| 6,406,719 B1 | 6/2002 | Farrar | |
| 6,565,777 B2 | 5/2003 | Farrar | |
| 6,677,304 B2 | 1/2004 | Di Napoli | |
| 6,713,081 B2 | 3/2004 | Robinson | |
| 6,809,077 B2 | 10/2004 | Or | |
| 6,814,966 B1 | 11/2004 | Wax | |
| 6,828,356 B2 | 12/2004 | Su | |
| 6,872,382 B1 | 3/2005 | Gamache | |
| 6,923,988 B2 | 8/2005 | Patel | |
| 6,953,776 B2 | 10/2005 | Di Napoli | |
| 6,979,671 B2 | 12/2005 | Or | |
| 6,982,282 B2 | 1/2006 | Lambert | |
| 6,984,628 B2 | 1/2006 | Bakhit | |
| 6,998,385 B2 | 2/2006 | Naicker | |
| 7,001,615 B1 | 2/2006 | Singh | |
| 7,012,064 B2 | 3/2006 | Or | |
| 7,012,065 B2 | 3/2006 | Or | |
| 7,026,290 B1 | 4/2006 | Domb | |
| 7,033,604 B2 | 4/2006 | Ueno | |
| 7,048,946 B1 | 5/2006 | Wong et al. | |
| 7,060,672 B2 | 6/2006 | Naicker | |
| 7,083,803 B2 | 8/2006 | Peyman | |
| 7,087,237 B2 | 8/2006 | Peyman | |
| 7,202,209 B2 | 4/2007 | Chang et al. | |
| 7,214,664 B2 | 5/2007 | Mitra | |
| 7,276,476 B2 | 10/2007 | Chang et al. | |
| 7,288,520 B2 | 10/2007 | Chang et al. | |
| 7,297,679 B2 | 11/2007 | Chang et al. | |
| 7,351,741 B2 | 4/2008 | Weidner | |
| 7,361,636 B2 | 4/2008 | Molino | |
| 7,378,391 B2 | 5/2008 | Molino | |
| 7,429,562 B2 | 9/2008 | Naicker | |
| 7,468,419 B2 | 12/2008 | Wu et al. | |
| 7,501,393 B2 | 3/2009 | Tien et al. | |
| 7,511,013 B2 | 3/2009 | Molino et al. | |
| 7,557,082 B2 | 7/2009 | Schiffman | |
| 7,632,807 B2 | 12/2009 | Molino et al. | |
| 7,655,625 B2 | 2/2010 | Brin | |
| 8,435,544 B2 * | 5/2013 | Mitra et al. | 424/400 |
| 2001/0041671 A1 | 11/2001 | Napoli | |
| 2003/0018044 A1 | 1/2003 | Peyman | |
| 2003/0044452 A1 | 3/2003 | Ueno | |
| 2003/0143277 A1 | 7/2003 | Ameye et al. | |
| 2003/0165545 A1 | 9/2003 | Huth | |
| 2004/0048777 A1 | 3/2004 | Weidner | |
| 2004/0106546 A1 | 6/2004 | Napoli | |
| 2004/0110666 A1 | 6/2004 | Or | |
| 2004/0156913 A1 | 8/2004 | Fang | |
| 2004/0266669 A1 | 12/2004 | Wu | |
| 2005/0014691 A1 | 1/2005 | Bakhit | |
| 2005/0031697 A1 | 2/2005 | Vehige et al. | |
| 2005/0048098 A1 | 3/2005 | Wong et al. | |
| 2005/0059583 A1 | 3/2005 | Acheampong | |
| 2005/0063996 A1 | 3/2005 | Peyman | |
| 2005/0063997 A1 | 3/2005 | Peyman | |
| 2005/0119160 A1 | 6/2005 | Keith | |
| 2005/0152980 A1 | 7/2005 | Ausborn | |
| 2005/0181018 A1 | 8/2005 | Peyman | |
| 2005/0191334 A1 | 9/2005 | Wong et al. | |
| 2005/0277584 A1 | 12/2005 | Tien | |
| 2006/0034799 A1 | 2/2006 | Brines | |
| 2006/0034892 A1 | 2/2006 | Ueno | |
| 2006/0052340 A1 | 3/2006 | Tsuzuki | |
| 2006/0067966 A1 | 3/2006 | Wong et al. | |
| 2006/0069015 A1 | 3/2006 | Molino | |
| 2006/0069016 A1 | 3/2006 | Molino | |
| 2006/0074015 A1 | 4/2006 | Molino | |
| 2006/0110428 A1 | 5/2006 | deJuan | |
| 2006/0116428 A1 | 6/2006 | Jimenez-Bayardo | |
| 2006/0148686 A1 | 7/2006 | Xia | |
| 2006/0177430 A1 | 8/2006 | Bhushan | |
| 2006/0183698 A1 | 8/2006 | Abelson | |
| 2006/0198871 A1 | 9/2006 | Wong | |
| 2006/0204543 A1 | 9/2006 | Wong et al. | |
| 2006/0204548 A1 | 9/2006 | Nivaggioli et al. | |
| 2006/0228414 A1 | 10/2006 | Cook | |
| 2006/0257450 A1 | 11/2006 | Mudumba | |
| 2006/0257451 A1 | 11/2006 | Varner | |
| 2006/0280774 A1 | 12/2006 | Wong et al. | |
| 2007/0015691 A1 | 1/2007 | Chang | |
| 2007/0015693 A1 | 1/2007 | Chang et al. | |
| 2007/0020336 A1 | 1/2007 | Loftsson et al. | |
| 2007/0043006 A1 | 2/2007 | Bingaman | |
| 2007/0078077 A1 | 4/2007 | Peyman | |
| 2007/0087962 A1 | 4/2007 | Tien | |
| 2007/0092539 A1 | 4/2007 | Jimenez-Bayardo | |
| 2007/0105761 A1 * | 5/2007 | Chappell et al. | 514/11 |
| 2007/0141115 A1 | 6/2007 | Kunzler | |
| 2007/0149447 A1 | 6/2007 | Chang et al. | |
| 2007/0167358 A1 | 7/2007 | Feinerman et al. | |
| 2007/0191266 A1 | 8/2007 | Brin | |
| 2007/0219127 A1 | 9/2007 | Walt | |
| 2007/0299004 A1 | 12/2007 | Acheampong et al. | |
| 2008/0009436 A1 | 1/2008 | Chang | |
| 2008/0021101 A1 | 1/2008 | Jimenez-Bayardo | |
| 2008/0039378 A1 | 2/2008 | Graham et al. | |
| 2008/0050420 A1 | 2/2008 | Wong | |
| 2008/0050421 A1 | 2/2008 | Wong | |
| 2008/0069859 A1 | 3/2008 | Wong | |
| 2008/0070834 A1 | 3/2008 | Chang | |
| 2008/0124377 A1 | 5/2008 | Wong et al. | |
| 2008/0146497 A1 | 6/2008 | Graham et al. | |
| 2008/0207494 A1 | 8/2008 | Chang et al. | |
| 2008/0207495 A1 | 8/2008 | Graham | |
| 2008/0249002 A1 | 10/2008 | Molino et al. | |
| 2009/0062249 A1 | 3/2009 | Wong | |
| 2009/0092665 A1 * | 4/2009 | Mitra et al. | 424/450 |
| 2009/0131307 A1 | 5/2009 | Tien et al. | |
| 2009/0148499 A1 | 6/2009 | Wong et al. | |
| 2009/0196905 A1 | 8/2009 | Spada et al. | |
| 2009/0264348 A1 | 10/2009 | Schiffman | |

FOREIGN PATENT DOCUMENTS

| | | |
|---|---|---|
| WO | WO 96/14829 | 5/1996 |
| WO | WO 00/40219 | 7/2000 |
| WO | WO 03/032949 | 4/2003 |
| WO | WO 03/033526 | 4/2003 |
| WO | WO 03/033527 | 4/2003 |
| WO | WO 03/051351 | 6/2003 |
| WO | WO 2004/089960 | 10/2004 |
| WO | WO 2004/096261 | 11/2004 |
| WO | WO 2006/001963 | 1/2006 |

(56) References Cited

FOREIGN PATENT DOCUMENTS

| WO | WO 2006/028361 | 3/2006 |
|---|---|---|
| WO | WO 2006/036614 | 4/2006 |
| WO | WO 2006/086744 | 8/2006 |
| WO | WO 2008/002118 | 1/2008 |
| WO | WO 2009/048929 | 4/2009 |

OTHER PUBLICATIONS

Cosar et al. Topical Cyclosporine in Pediatric Keratoplasty. Eye & Contact Lens, vol. 29(2)103-107, (Apr. 2003).

delAmo, E. et al., Current and Future Ophthalmic Drug Delivery Systems: A Shift to the Posterior Segment, *Drug Discovery Today*, vol. 13, Nos. 3/4, pp. 135-143 (Feb. 2008).

Dumont et al. The Immunosuppressive and Toxic Effects of FK-506 Are Mechanistically Related: Pharmacology of a Novel Antagonist of FK-506 and Rapamycin. Journal of Experimental Medicine, vol. 176(3):751-60, (Sep. 1, 1992).

Feske et al. $Ca^{2+}$/Calcineurin Signalling in Cells of the Immune System. Biochemical and Biophysical Research Communications vol. 311(4):1117-1132, (Nov. 28, 2003).

Granelli-Piperno, A. et al., Lymphokine and Nonlymphokine mRNA Levels in Stimulated Human T Cells, *J. Exp. Med.*, vol. 163, pp. 922-937 (Apr. 1986).

Gummert et al. Newer Immunosuppressive Drugs: A Review. Journal of the American Society of Nephrology, vol. 10(6):1366-80, (Jun. 1999).

Hackett et al., Assessing Ocular Irritation. *Dermatoxicology*, $5^{th}$ Edition, edited by F.N. Marzulli and H.I. Maibach. Washington, D.C.: Taylor & Francis Publishers, Chapter 44, pp. 557-571 (1996).

Hackett et al., Opthalmic Toxicology. *Dermatoxicology*, $5^{th}$ Edition, edited by F.N. Marzulli and H.I. Maibach. Washington, D.C.: Taylor & Francis Publishers, Chapter 23, pp. 299-306 (1996).

Hackett et al., Eye Irritation. *Dermatoxicology*, $4^{th}$ Edition, edited by F.N. Marzulli and H.I. Maibach. Washington, D.C.: Hemisphere Publishing Corporation, Chapter 31, pp. 749-815 (1991).

Henriksen et al. Bioadhesion of Hydrated Chitosans: An In Vitro and In Vivo Study. International Journal of Pharmaceutics. vol. 145(1-2):231-240, (Dec. 6, 1996).

Hu, X. et al., Biodegradable Amphiphilic Polymer-Drug Conjugate Micelles, *Expert Opin. Drug Deliv.*, vol. 6, No. 10, pp. 1079-1090 (Oct. 2009).

Hughes, P. et al., Topical and Systemic Drug Delivery to the Posterior Segments, *Advanced Drug Delivery Reviews*, vol. 57, pp. 2010-2032 (Nov. 10, 2005).

Izci et al. Histologic Characteristics and Local Cellular Immunity of the Gland of the Third Eyelid After Topical Ophthalmic Administration of 2% Cyclosporine for Treatment of Dogs With Keratoconjunctivitis Sicca. American Journal of Veterinary Research, vol. 63(5):688-694, (May 2002).

Kaswan et al. Spontaneous Canine Keratoconjunctivitis Sicca. A Useful Model for Human Keratoconjunctivitis Sicca: Treatment With Cyclosporine Eye Drops. Archives of Ophthalmology, vol. 107(8):1210-1216, (Aug. 1989).

Kaur, I. et al., Ocular Preparations: The Formulation Approach, *Drug Development and Industrial Pharmacy*, vol. 28, No. 5, pp. 473-493 (May 2002).

Koevary, Steven, Pharmacokinetics of Topical Ocular Drug Delivery: Potential Uses for the Treatment of Diseases of the Posterior Segment and Beyond, *Current Drug Metabolism*, vol. 4, No. 3., pp. 213-222 (Jun. 2003).

Komai, Y. et al., The Three-Dimensional Organization of Collagen Fibrils in the Human Cornea and Sclera, *Investigative Ophthalmology & Visual Science*, vol. 32, No. 8, pp. 2244-2258 (Jul. 1991).

Liu et al. Calcineurin is a Common Target of Cyclophilin-Cyclosporin A and FKBP-FK506 Complexes. Cell, vol. 66(4):807-815, (Aug. 23, 1991).

Loftsson, T., et al., Topical Drug Delivery to the Posterior Segment of the Eye: Anatomical and Physiological Considerations, *Pharmazie*, vol. 63, No. 3, pp. 171-179 (Mar. 2008).

Lukyanov and Torchilin: *Micelles from lipid derivatives of water-soluble polymers as delivery systems for poorly doluble drugs*, Advanced Drug Delivery Reviews 56, 1273-1289, (May 2004).

Lukyanov et al. Polyethylene Glycol-Diacyllipid Micelles Demonstrate Increased Accumulation in Subcutaneous Tumors in Mice. *Pharmaceutical Research*. vol. 19(10): 1424-1429, (Oct. 2002).

Mu et al. Mixed Micelles Made of Poly(Ethylene Glycol)—Phosphatidylethanolamine Conjugate and D-A-Tocopheryl Polyethylene Glycol 1000 Succinate as Pharmaceutical Nanocarriers for Camptothecin. International Journal of Pharmaceutics, vol. 306(1-2):142-149, (Dec. 8, 2005).

Olivero et al. Clinical Evaluation of 1% Cyclosporine for Topical Treatment of Keratoconjunctivitis Sicca in Dogs. Journal of the American Veterinary Medical Association, vol. 199(8):1039-1042, (Oct. 15, 1991).

Pal Kaur and Smitha: *Penetration Enhancers and Ocular Bioadhesives: Two New Avenues for Ophthalmic Drug Delivery*, Drug Development and Industrial Pharmacy, 28(4), 353-369 (May 2002).

Rabinovich-Guilatt, L., et al., Cationic Vectors in Ocular Drug Delivery, *Journal of Drug Targeting*, vol. 12, No. 9-10, pp. 623-633 (Dec. 2004).

Robert et al. Experimental-Method for Bioadhesive Testing of Various Polymers. Acta Pharmaceutica Technologica-International Journal of Drug Formulation and Biopharmaceutics, vol. 34(2):95-98, (Jun. 1988).

Rusnak & Mertz. Calcineurin: Form and Function. Physiological Reviews, vol. 80(4):1483-1521, (Oct. 2000).

Stepkowski, Stanislaw M., Molecular Targets for Existing and Novel Immunosuppressive Drugs, *Expert Reviews in Molecular Medicine*, vol. 2, No. 4, pp. 1-23 (Jun. 21, 2000).

Sugita et al. A New Calcineurin Inhibitor, Pimecrolimus, Inhibits the Growth of *Malassezia* Spp. Antimicrobial Agents and Chemotherapy, vol. 50(8):2897-2898, (Aug. 2006).

Tobyn et al. Factors Affecting In-Vitro Gastric Mucoadhesion .1. Test Conditions and Instrumental Parameters. European Journal of Pharmaceutics and Biopharmaceutics. vol. 41(4):235-241, (Aug. 1995).

Tobyn et al. Factors Affecting In-Vitro Gastric Mucoadhesion .2. Physical Properties of Polymers. European Journal of Pharmaceutics and Biopharmaceutics. vol. 42(1):56-61, (Jan. 1996).

Torchilin, V.P., Micellar Nanocarriers: Pharmaceutical Perspectives, *Pharmaceutical Research*, vol. 24, No. 1, pp. 1-16 (Jan. 2007).

Wu and Hopkins. Characteristics of D-Alpha-Tocopheryl PEG 1000 Succinate for Applications as an Absorption Enhancer in Drug Delivery Systems. Pharmaceutical Technology, vol. 23(10):52-60. (Oct. 1999).

International Search Report based on PCT/US08/79170 dated Dec. 31, 2008.

Borchard et al., "The Potential of Muco-Adhesive Polymers in Enhancing Intestinal Peptide Drug Absorption. III: Effects of Chitosan-Glutamate and Carbomer on Epithelial Tight Junctions In Vitro," *Journal of Controlled Release*, 39(2-3), pp. 131-138 (May 1996).

Burglassi et al., "Development and In Vitro/In Vivo Testing of Mucoadhesive Buccal Patches Releasing Benzydamine and Lidocaine," *International Journal of Pharmaceuticals*, 133(1-2), pp. 1-7 (May 14, 1996).

Fuongfuchat et al., "Rheological Studies of the Interaction of Mucins with Alginate and Polyacrylate," *Carbohydrate Research*, 284(1), pp. 85-99 (Apr. 18, 1996).

Rambali et al., "Influence of the Roll Compactor Parameter Settings and the Compression Pressure on the Buccal Bio-Adhesive Tablet Properties," *International Journal of Pharmaceuticals*, 220(1), pp. 129-140 (Jun. 4, 2001).

Weyenberg et al., "Characterization and In Vivo Evaluation of Ocular Minitablets Prepared with Different Bioadhesive Carbopol-Starch Components," *European Journal of Pharmaceutics and Biopharmaceutics*, 62(2), pp. 202-209 (Feb. 2006).

(56) References Cited

OTHER PUBLICATIONS

International Search Report based on PCT/US10/33779 mailed Jun. 29, 2010.
Mitra, "Role of Transporters in Ocular Drug Delivery System", *Pharmaceutical Research*, vol. 26, No. 5, 17, pp. 1192-1196, Mar. 2009.
Janoria et al., "Novel approaches to retinal drug delivery", *Expert Opinion on Drug Delivery, Informa Healthcare, GB*, vol. 4, pp. 371-388, Jul. 2007.
Extended European Search Report in EP Serial No. 10786539.6 mailed Nov. 9, 2012.

* cited by examiner

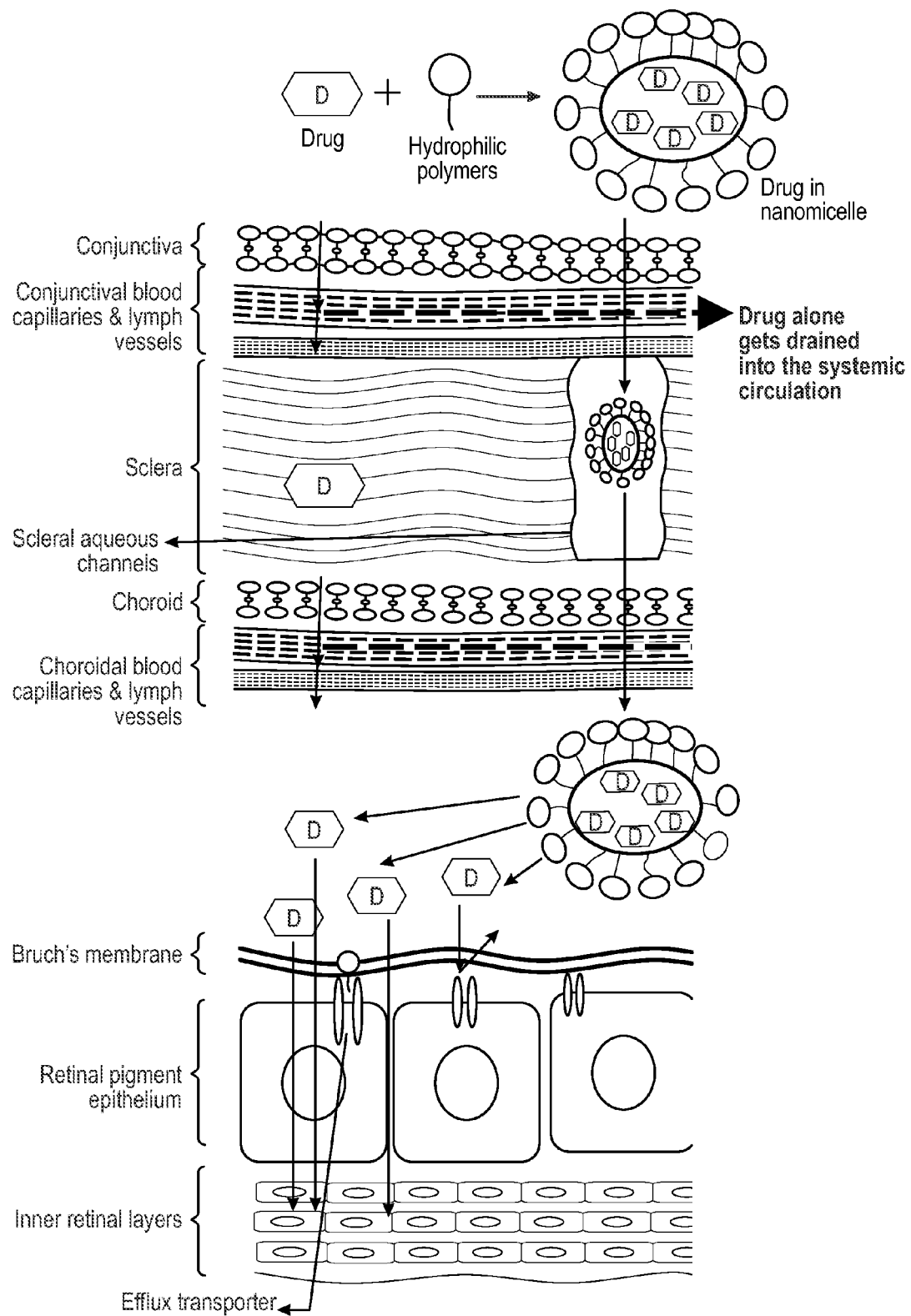

TOPICAL DRUG DELIVERY SYSTEMS FOR OPHTHALMIC USE

RELATED APPLICATIONS

This application claims the benefit of and priority to U.S. Provisional Application Ser. No. 61/185,396, filed Jun. 9, 2009, the entirety of this application is hereby incorporated herein by reference.

FIELD

The embodiments disclosed herein relate to topical drug delivery systems, and more particularly to mixed nanomicellar formulations of corticosteroids and methods of treating diseases affecting the posterior ocular segments.

BACKGROUND

The opthalmology market includes front-of-eye conditions such as glaucoma, where drugs can be delivered using eye drops and other conventional ophthalmic formulations; and retinal diseases affecting the vitreous or back-of-the-eye, such as age-related macular degeneration (AMD) and diabetic macular edema (DME), which are the leading causes of vision loss in the western world.

Disease and injury to the anterior surface of the eye are the leading causes of visits to physicians for medical eye care in the United States. These diseases and injuries rank among the most painful of eye conditions and can lead to disability and blindness. Major clinical problems of the surface of the eye include ocular surface drying, tear film abnormalities, and related complications; ocular surface wounds with resultant pathology and scarring; corneal dysfunction dystrophies and inherited disease; inflammatory disease; and external ocular infections. Eye diseases and injuries can have symptoms ranging from itchy, runny eyes to impaired vision. Therefore, it is important to address eye problems right away, as some diseases can progressively worsen or even trigger other serious problems. Most pharmacologic management of ocular disease includes the topical application of solutions to the surface of the eye as drops. Despite the relatively small proportion of a topically applied drug dose that ultimately reaches anterior segment ocular tissues, topical formulations remain effective, largely because of the very high concentrations of drugs that are administered.

Disease and injury to tissues of the posterior segment of the eye, including the retina and choroid, is involved in many of the most common blinding diseases in the industrialized world. Age-related macular degeneration (AMD) alone impacts more than 10 million Americans. Severe vision loss from AMD and other diseases affecting the posterior segment, including diabetic retinopathy, glaucoma, and retinitis pigmentosa account for most cases of irreversible blindness world wide. Currently, the treatment of posterior segment disease is to a significant extent limited by the difficulty in delivering effective doses of drugs to target tissues in the posterior eye. While new drugs have emerged for the treatment of these diseases, the current standard of care is administration by direct injection into the vitreous. This kind of regime is not only hard for patients to endure but carries a growing risk of tissue damage and infection. Topical drops rarely make it to the back-of-the-eye and a blood-ocular barrier prevents systemically administered drugs from penetrating ocular tissue.

SUMMARY

The embodiments disclosed herein relate to topical drug delivery systems for ophthalmic use, including mixed nanomicellar formulations of corticosteroids and methods of treating diseases affecting the posterior ocular segments.

According to aspects illustrated herein, there is disclosed an aqueous ophthalmic solution that includes nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v. In an embodiment, the aqueous ophthalmic solution has a pH of 6.6 to 7.0.

According to aspects illustrated herein, there is disclosed an eye drop formulation that includes a corticosteroid at a concentration ranging from about 0.01% w/v to about 1.00% w/v; vitamin E TPGS at a concentration ranging from about 3.0% w/v to about 5.0% w/v; and octoxynol-40 at a concentration ranging from about 1.0% w/v to about 3.0% w/v, wherein the corticosteroid is solubilized through entrapment in a mixed micellar hydrophobic core of the vitamin E TPGS and the octoxynol-40. In an embodiment, after administration of a single dose of the eye drop formulation to a rabbit, dexamethasone tissue levels in posterior retina-choroid are equivalent to concentrations of at least 30 ng/g.

According to aspects illustrated herein, there is disclosed a kit that includes a unit dose of an aqueous ophthalmic solution comprising nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v, wherein the unit dose is contained within a vial prepared from a pharmaceutically acceptable packaging material. In an embodiment, the unit dose is about 50 µL.

According to aspects illustrated herein, there is disclosed a method of treating a back-of-the-eye ocular condition that includes administering to an eye of a patient an effective amount of an aqueous ophthalmic solution comprising nanomicelles in a physiologically acceptable buffer, having a pH of 5.0 to 8.0, wherein a corticosteroid at a concentration ranging from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 2.0% w/v to about 5.0% w/v stabilized with octoxynol-40 at a concentration ranging from about 1.0% w/v to about 3.0% w/v.

According to aspects illustrated herein, there is disclosed a method of treating a back-of-the-eye disease that includes topically applying a formulation of the present disclosure to the eye, the formulation comprising an aqueous solution of corticosteroid-loaded nanomicelles; transporting the corticosteroid-loaded nanomicelles by passive diffusion through the aqueous channels/pores of the sclera; transporting the corticosteroid-loaded nanomicelles by endocytosis through the choroid to the basolateral side of the retinal pigment epithelium; discharging the corticosteroid from the nanomicelles into the retinal pigment epithelium; and treating the back-of-the-eye disease.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1 is a schematic representation of an embodiment of the permeation of a topically applied hydrophobic drug through water channels/pores of the sclera of the eye and evasion of conjunctival/choroidal blood vessels and lymphatics using a formulation of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The presently disclosed embodiments relate to nonirritating mixed nanomicelles comprising water-insoluble (hydrophobic) drugs. Solubilization of the hydrophobic drug is achieved through entrapment in a mixed micellar hydrophobic core with a corona composed of hydrophilic chains extending from the hydrophobic core. In an embodiment, the nanomicelles are composed of two non-ionic surfactants; a first non-ionic surfactant with an HLB index greater than about 10 and a second non-ionic surfactant with an HLB index of greater than about 13, at a defined ratio. In an embodiment, the absolute difference between the HLB index of the first non-ionic surfactant and the HLB index of the second non-ionic surfactant is greater than about 3. In an embodiment, the first non-ionic surfactant acts as the main spherical structure and the second non-ionic surfactant adds strength to the nanomicellar structure by inserting itself between two polymeric chains of the first non-ionic surfactant. In an embodiment, a suitable carrier for the nanomicelles is an aqueous solution. Such stabilization is believed to result in the formation of aqueous solutions of extremely hydrophobic drugs that have optical clarity. An aqueous solution of nanomicelles of the present disclosure may comprise other components, including, but not limited to, a buffering agent, an isotonicity, a surfactant, a chelating agent, an antibacterial agent, an anti-infective agent, a diagnostic agent and a preservative. Collectively, an aqueous solution of mixed nanomicelles of the present disclosure, which optionally include other components (as described above), is known as a "formulation" of the present disclosure.

In an embodiment, mixed nanomicelles of the present disclosure carry at least one corticosteroid. In an embodiment, the at least one corticosteroid is selected from the group consisting of prednisolone, methylprednisolone, prednisone, triamcinolone, betamethasone, budesonide, and dexamethasone. In an embodiment, mixed nanomicelles of the present disclosure carry the corticosteroid dexamethasone. In an embodiment, mixed nanomicelles of the present disclosure can substantially improve the solubility and bioavailability of the corticosteroid. In an embodiment, mixed nanomicelles of the present disclosure comprising dexamethasone can improve the solubility of dexamethasone by up to about 10 fold.

In an embodiment, mixed nanomicelles of the present disclosure, with a size ranging from about 10 nm to about 20 nm, allow for efficient accumulation of the corticosteroid into targeted diseased tissues. In an embodiment, an aqueous solution of mixed nanomicelles of the present disclosure can be used as a topically applied drug delivery platform for delivery of a corticosteroid to the back of the eye. Solutions may be manually delivered to the eye in suitable dosage form, e.g., eye drops, or delivered by suitable microdrop or spray apparatus typically affording a metered dose of medicament. It has been found that after topical administration of a formulation of the presently disclosed embodiments, the corticosteroid is able to reach the back of the eye. As will be shown in the Examples below, significantly high levels of dexamethasone were found at the back of the eye without resulting in significant levels in the lens and vitreous humor, suggesting the corticosteroid is not reaching the back of the eye via a conventional pathway of going through the eye. Instead, it is believed that the drug is being transferred to the back of the eye via an unconventional pathway of going around the eye. Therefore, a formulation of the presently disclosed embodiments is particularly useful for topical application to the eye of a patient for the treatment of back-of-the-eye ocular conditions.

In an embodiment, a formulation of the present disclosure is applied topically to an eye. In an embodiment, a formulation of the present disclosure is used to treat, reduce, prevent, ameliorate and alleviate ocular conditions in a patient or subject. In an embodiment, a formulation of the present disclosure is used in the treatment of a posterior segment disorder and disease. In an embodiment, a formulation of the present disclosure is used for the treatment of a back-of-the-eye (posterior) ocular condition, including, but not limited to, idiopathic uveitis, ocular surface inflammation, age-related macular degeneration (AMD, wet and dry), diabetic eye conditions including diabetic retinopathy and maculopathy, macular edema, glaucoma, optic neuritis, ocular hypertension, post-operative eye pain and inflammation, posterior segment neovascularization (PSNV), proliferative vitreoretinopathy (PVR), hypertensive retinopathy, cytomegalovirus retinitis (CMV), choroidal neovascular membranes (CNVM), vascular occlusive diseases, retinitis pigmentosa, neuralgia, aging (e.g. muscle relaxants and other aesthetic products), cicatrizing ocular surface diseases, ocular infections, inflammatory ocular diseases, ocular surface diseases, corneal diseases, retinal diseases, ocular manifestations of systemic diseases, hereditary eye conditions, and ocular tumors.

It has been found that after topical administration of a formulation of the present disclosure, the drug is able to reach the posterior of the eye. There are two potential pathways for molecules to reach posterior eye tissues following topical administration: (1) intraocular route through the cornea, aqueous humor, lens, vitreous humor and finally retina; and (2) trans-scleral route around the conjunctiva, through the sclera, choroid, and retina. For hydrophobic drugs, the intraocular route is often unsuccessful since the hydrophilic stroma becomes a rate limiting barrier for trans-corneal absorption. Moreover, aqueous humor in the anterior and posterior segments flow in opposite directions and hinder the passage of molecules from the aqueous humor to the lens and, subsequently, through the lens zonular spaces to the vitreous humor, thus making this an unfavorable pathway. The trans-scleral route offers a more viable pathway for back-of-the-eye delivery of hydrophobic molecules by passive diffusion through the scleral water channels/pores.

Water-insoluble drugs, like dexamethasone, encapsulated in mixed nanomicelles, form spherical structures of amphiphilic molecules in water. FIG. 1 is a schematic representation of an embodiment of the permeation of a topically applied water-insoluble drug through water channels/pores of the sclera of the eye and evasion of conjunctival/choroidal blood vessels and lymphatics using an aqueous solution of mixed nanomicelles of the present disclosure. In an embodiment, a method of treating a back-of-the-eye ocular condition includes administering (for example, topically applying) a formulation of the present disclosure to the eye, the formulation comprising an aqueous solution of water-insoluble drug-loaded nanomicelles; transporting the water-insoluble drug-loaded nanomicelles by passive diffusion through the aqueous channels/pores of the sclera; transporting the water-insoluble drug-loaded nanomicelles by endocytosis through the choroid to the basolateral side of the retinal pigment epithelium; discharging the water-insoluble drug from the nanomicelles into the retinal pigment epithelium; and treating the back-of-the-eye disease. In an embodiment, hydrophilic chains in the nanomicellar corona partially evade wash-out by the conjunctival/choroidal blood vessels and lymphatics. In an embodiment, limited intraocular drug penetration is achieved as a result of the topical application of the formulation of the present disclosure. In an embodiment, the limited intraocular drug penetration results in negligible concentration of the water-insoluble drug in the lens and vitreous humor of the eye. In an embodiment, the limited intraocular drug penetration results in the intraocular pressure (IOP) remaining substantially the same, i.e., no increase in IOP due to the topical application of the formulation. In an embodiment, the limited intraocular drug penetration results in no cataract development.

The outer surface of the mixed nanomicellar structure protrudes hydrophilic —OH groups to the outside environment. It is believed that due to their hydrophilic corona, these micellar nanocarriers can pass through the aqueous channels/pores of the sclera, which range from about 30 nm to about 300 nm in size. Nanomicelles may then be absorbed onto the basolateral side of the Retinal Pigment Epithelium (RPE) through endocytosis. The contents of the micellar nanocarriers are discharged inside the cell after fusion with the cell membrane. It is also believed that during the transit, the hydrophilic nanomicellar corona helps to evade drug wash-out into the systemic circulation by the conjunctival/choroidal blood vessels and lymphatics. In an embodiment, a formulation of the present disclosure is able to carry hydrophobic drug molecules in therapeutic amounts to the retina, Bruch's membrane and RPE. Since the mixed nanomicelles can carry the hydrophobic drugs preferentially across conjunctiva and sclera rather than across cornea, lens, and vitreous, negligible levels or no detectable levels are observed in the lens and vitreous. Therefore, the formulations of the presently disclosed embodiments are particularly useful for topical application to the eye of a patient for the treatment of back-of-the-eye (posterior) ocular conditions.

A patient or subject to be treated by a formulation of the present disclosure can mean either a human or a non-human animal. In an embodiment, the disclosure provides methods for treatment of back-of-the-eye ocular conditions in a human patient in need thereof. In an embodiment, the disclosure provides methods for treatment of back-of-the-eye ocular conditions in a veterinary patient in need thereof, including, but not limited to dogs, horses, cats, rabbits, gerbils, hamsters, rodents, birds, aquatic mammals, cattle, pigs, camelids, and other zoological animals.

As used herein, the terms "micelle" and "nanomicelle" refer to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a "mixed micelle". Nanomicelles are colloidal particles with nanometer size ranges, forming spherical structures of amphiphilic molecules in water.

Polymeric micelles are exploited as pharmaceutical nanocarriers for the delivery of poorly water-soluble drugs, which can be solubilized in the hydrophobic inner core of a micelle. Micelles can therefore serve to improve solubility and bioavailability of various hydrophobic (water-insoluble) drugs. (Lukynov et al., Polyethylene glycol-diacyllipid micelles demonstrate increased accumulation in subcutaneous tumors in mice. Pharm. Res. 2002, 19:1424-1429.) The small size (typically about 10 to 100 nm) of micelles allows the advantage of sterilization of micelles by filtration through membranes with the cut off size 0.22 µm. Another example of a mixed micellar formulation is described, for example, by Mu et al., 2005, comprising polyethylene glycol phosphatidylethanolamine conjugate and vitamin E TPGS in a mixed micellar formulation of the poorly soluble anticancer drug camptothecin. (Mu et al., Int. J. Pharmaceutics 2005, 306:142-149). Micelles can be formed from one or more polymeric nonionic surfactants. Since the micelle size is smaller than light wavelengths the light is not scattered by the small micelles resulting in a transparent optically clear solution.

As used herein, the term "LX214" refers to a 0.2% topical formulation of the potent calcineurin inhibitor, voclosporin. The topical formulation is a non-irritating aqueous solution of mixed nanomicelles, the nanomicelles comprising a mixture of defined amounts of octoxynol-40 with vitamin E TPGS. In an embodiment, the topical formulation has optical clarity. In an embodiment, the average nanomicelle size ranges from about 10 nm to about 30 nm, from about 12 nm to about 28 nm, from about 14 nm to about 26 nm, from about 16 nm to about 24 nm, from about 18 nm to about 22 nm.

As used herein, the term "optical clarity" is defined as 90% or greater transmission of light of 400 nm wavelength in a 1.0 centimeter path. An aqueous ophthalmic solution of the present disclosure has a high degree of optical clarity. The optical clarity of the solution results from the nanomiceller size which is typically smaller than the smallest wavelength of a visible light radiation (about 350 nm). In an embodiment, the formulations of the present disclosure are substantially clear with an absorption loss less then about 0.1% per micron of path length. In an embodiment, the formulations of the present disclosure are substantially clear with an absorption loss less then about 0.05% per micron of path length measured at 400 nm.

The HLB (hydrophilic/lipophilic balance) index value is a concept introduced by Griffin in 1950 as a measure of the hydrophilicity or lipophilicity of nonionic surfactants. The HLB index value can be determined experimentally by the phenol titration method of Marszall; see "Parfumerie, Kosmetik", Vol. 60, 1979, pp. 444-448; further literature references can be found in Rompp, Chemistry Lexicon, 8th Edition 1983, p. 1750. See also, for example, U.S. Pat. No. 4,795,643 (Seth).

By "treating" or "treatment" is meant medically managing a subject (e.g., a patient) with the intent that a prevention, cure, stabilization, or amelioration of the symptoms will result. Treatment includes active treatment, that is, treatment directed specifically towards improvement of the disease; palliative treatment, that is, treatment designed for the relief of symptoms rather than the curing of the disease; preventive treatment, that is, treatment directed to prevention of the disease; and supportive treatment, that is, treatment employed to supplement another specific therapy directed toward the improvement of the disease. As such, "treatment" also refers to delaying the onset of the disease or disorder, or inhibiting the disease or disorder, thereby providing a prophylactic benefit.

In the embodiments disclosed herein, a therapeutically effective amount is applied topically to the eye of a subject in need of treatment. A "therapeutically effective amount" refers to an amount of the therapeutic agent either as an individual compound or in combination with other compounds that is sufficient to induce a therapeutic effect or prophylactic benefit on the disease or condition being treated. This phrase should not be understood to mean that the dose must completely eradicate the ailment. A therapeutically effective amount will vary depending on, inter alia, the pharmacological properties of the compound used in the methods, the condition being treated, the frequency of administration, the mode of delivery, characteristics of the individual to be treated, the severity of the disease, and the response of the patient.

To treat the ocular disease, the formulations of the present disclosure can be applied topically to the affected eye(s). In some embodiments, the ocular formulation can be applied in defined volumes, such about 10, 20, 35, 50, 75, 100, 150, or 200 μl or more. The frequency of application will depend on, among others, the type of ocular disease being treated, the severity of the condition, age and sex of the patient, the amount of the water-insoluble drug in the formulation, and the pharmacokinetic profile in the ocular tissue to be treated. In some embodiments, the formulation can be administered more than one times per day. When the formulations are administered more than once per day, the frequency of administration can be two, three, four, up to eight times per day. In some embodiments, the formulation can be administered one to four times daily. In some embodiments, the formulation can be applied once every two days. In some embodiments, the formulation can be applied once every four days. In some embodiments, the formulation can be administered once every week. Determining the frequency and amount to be administered for a particular ocular disorder is well within the skill and judgment of the attending practitioner.

In some embodiments, an ocular formulation of the present disclosure can be provided in the form of a kit. As such, the kit can contain the ocular formulation in a container, a vial, as single dose unit or as a single solution reservoir. The kit can also contain a dispenser for dispensing measured doses as well as instructions for dosing and use of the formulations. In an embodiment, the kit assembly also provides a sequential dispenser means containing a plurality of daily sets of kit sub-assembly components, such as a series of jars, bottles, containers or ampoules containing a supply (unit dose) of formulation.

In an embodiment, a formulation of the present disclosure comprises from about 0.01% w/v to about 80% w/v, from about 0.05% w/v to about 16% w/v, from about 0.10% w/v to about 3.2% w/v, from about 0.15% w/v to about 0.60% w/v of the water-insoluble drug. In an embodiment, a formulation of the present disclosure comprises about 0.20% w/v of the water-insoluble drug. In an embodiment, a formulation of the present disclosure comprises about 0.10% w/v of the water-insoluble drug. Suitable classes of water-insoluble drugs include, but are not limited to, peptides, cyclic peptides (e.g., some calcineurin inhibitors), eicosanoids (e.g. prostacyclins and prostaglandins), anti-inflammatory drugs, immunosuppressive drugs (e.g., some mTOR inhibitors), autonomic drugs (e.g. beta-blockers, alpha-blockers, beta-agonists, and alpha-agonists), antiangiogenic drugs, biologics, gene therapy agents (e.g., viral vectors), anti-infectives (e.g anti-fungals, antibiotics, and antivirals), monoclonal antibodies and fragments thereof, retinoids, RNAi, photo sensitizers, steroids (e.g., corticosteroids), mixture drugs, immuno-modulators, chemotherapeutic agents, G-coupled protein receptor antagonists, receptor tyrosine kinase (RTK) inhibitors, growth hormone inhibitors, integrin inhibitors, Sdfl/CXCR4 pathway inhibitors, nACh receptor antagonists, analogs thereof or pharmaceutically acceptable salts, esters or prodrugs. In an embodiment, the water-insoluble drug is selected from one of cyclosporin A, voclosporin, ascomycin, tacrolimus (FK506), sirolimus (rapamycin), pimecrolimus, dexamethasone, an analog thereof or a pharmaceutically acceptable salt, ester or prodrug. In an embodiment, the water-insoluble drug is a calcineurin inhibitor. In an embodiment, the calcineurin inhibitor is voclosporin. In an embodiment, the water-insoluble drug is an mTOR inhibitor. In an embodiment, the mTOR inhibitor is rapamycin. In an embodiment, the water-insoluble drug is a corticosteroid. In an embodiment, the corticosteroid is dexamethasone. The formulations can further include pharmaceutical excipients, including, but not limited to, antibacterial agents, anti-infective agents, diagnostic agents and preservatives.

Calcineurin Inhibitors

Calcineurin is a calcium/calmodulin-regulated protein phosphatase involved in intracellular signaling. For reviews on calcineurin, see e.g. Rusnak and Mertz, Physiol. Rev. 80, 1483-1521 (2000) and Feske et al., Biochem. Biophys. Commun. 311, 1117-1132 (2003). Calcineurin inhibitors are substances which block calcineurin dephosphorylation of appropriate substrates, by targeting calcineurin phosphatase (PP2B, PP3), a cellular enzyme that is involved in gene regulation. Calcineurin inhibitors have been found to be effective in inhibiting, among other things, T-cell proliferation, and this mode of action contributes to clinical effects of calcineurin inhibitors to treat chronic inflammation and act as immunosuppressants.

A calcineurin inhibitor of the present disclosure is preferably an immunophilin-binding compound having calcineurin inhibitory activity. Immunophilin-binding calcineurin inhibitors are compounds forming calcineurin inhibiting complexes with immunophilins, e.g. cyclophilin and macrophilin. Examples of cyclophilin-binding calcineurin inhibitors are cyclosporins or cyclosporin derivatives (hereinafter cyclosporins) and examples of macrophilin-binding calcineurin inhibitors are ascomycin and ascomycin derivatives (hereinafter ascomycins), see e.g. Liu et al., Cell 66, 807-815 (1991) and Dumont et al., J. Exp. Med., 176, 751-780 (1992). Ascomycins and their preparation are known. Ascomycin (FR 520) is a macrolide antibiotic disclosed e.g. in U.S. Pat. No. 3,244,592 and in EP 349061. A wide range of ascomycin derivatives are known, which are either naturally occurring among fungal species or are obtainable by manipulation of fermentation procedures or by chemical derivatization. Ascomycin-type macrolides include ascomycin, tacrolimus (FK506) and pimecrolimus.

Cyclosporin is a fungal peptide composed of 11 amino acids. It has been in use since 1983 as an immunosuppressive drug. Cyclosporin inhibits the production of IL-2. Cyclosporin binds to the cytosolic protein cyclophilin (an immunophilin) of immunocompetent lymphocytes, especially T-lymphocytes. The complex of cyclosporin and cyclophilin inhibits calcineurin, which under normal circumstances induces the transcription of interleukin-2 Cyclosporin also inhibits lymphokine production and interleukin release, leading to a reduced function of effector T-cells. Cyclosporin is used in the treatment of acute rejection reactions, but has been increasingly substituted with newer immunosuppressants due to nephrotoxicity.

Cyclosporins and their preparation are e.g. disclosed in U.S. Pat. No. 4,117,118. Cyclosporin, originally extracted from the soil fungus *Potypaciadium infilatum*, has a cyclic 11-amino acid structure and includes e.g. Cyclosporins A through I, such as Cyclosporin A, B, C, D and G. Cyclosporin A (cyclosporine; cyclo(L-alanyl-D-alanyl-N-methyl-L-leucyl-N-methyl-L-leucyl-N-methyl-L-valyl-((3R,4R,6E)-6,7-didehydro-3-hydroxy-N,4-dimethyl-L-2-aminooctanoyl-L-2-aminobutanoyl-N-methylglycyl-N-methyl-L-leucyl-L-valyl-N-methylleucyl)) is utilized in a commercially available ophthalmic emulsion (Ding et al., U.S. Pat. No. 5,474,979, Restasis®) used in the treatment of dry eye syndrome. Domb (U.S. Pat. No. 7,026,290) discloses a dispersible concentrate for the delivery of cyclosporin including a surfactant with an HLB (hydrophilic/lipophilic balance) of at least about 8 and a surfactant with a low HLB of less than about 5.

Cyclosporins of the present disclosure also include cyclosporin analogs. For example, cyclosporin analogs disclosed in Naicker et al., U.S. Pat. No. 6,998,385, incorporated herein by reference, are of particular interest. A preferred example of a cyclosporin analog is voclosporin (Cyclosporin A, 6((2S,3R,4R)-3-hydroxy-4-methyl-2-(methylamino)-6,8-nonadienoic acid)-; including specifically the trans-version ISA$_{Tx}$247, trans-ISA247 CAS RN 368455-04-3), which is described in, for example, Naicker et al., U.S. Pat. No. 7,429,562, incorporated herein by reference. Further compositions of voclosporin are described, for example, in Naicker et al., U.S. Pat. No. 7,060,672; incorporated by reference.

Voclosporin ("VCS") is a next-generation calcineurin inhibitor. Like other molecules of this class, VCS reversibly inhibits immunocompetent lymphocytes, particularly T-lymphocytes, and also inhibits lymphokine production and release. This action is primarily mediated through inhibition of calcineurin, a phosphatase enzyme found in the cytoplasm of cells. VCS is a more potent and less toxic semi-synthetic derivative of Cyclosporine A.

Tacrolimus (FK506) is another calcineurin inhibitor which is also a fungal product, but has a macrolide lactone structure. Tacrolimus (Prograf®, oral, injectable, Astellas Pharma US; and Protopic®, topical, Astellas Pharma US) is used as an immunosuppressant in conjunction with liver, kidney, heart, lung and heart/lung transplants. Tacrolimus also inhibits the production of IL-2. Tacrolimus binds to an immunophilin (FK-binding protein 12, FKBP12), followed by binding of the complex to calcineurin to inhibit its phosphatase activity.

Ascomycin, also called Immunomycin, FR-900520, FK520, is an ethyl analog of tacrolimus (FK506) with strong immunosuppressant properties. Ascomycin acts by binding to immunophilins, especially macrophilin-12. It appears that Ascomycin inhibits the production of Th1 (interferon- and IL-2) and Th2 (IL-4 and IL-10) cytokines Additionally, ascomycin preferentially inhibits the activation of mast cells, an important cellular component of the atopic response. Ascomycin produces a more selective immunomodulatory effect in that it inhibits the elicitation phase of allergic contact dermatitis but does not impair the primary immune response when administered systemically.

Pimecrolimus is an immunomodulating agent used in the treatment of atopic dermatitis (eczema). It is currently available as a topical cream, once marketed by Novartis (however Galderma is promoting the molecule in Canada since early 2007) under the trade name Elidel. Pimecrolimus is an ascomycin macrolactam derivative. Pimecrolimus, like tacrolimus, belongs to the ascomycin class of macrolactam immunosuppressives, acting by the inhibition of T-cell activation by the calcineurin pathway and inhibition of the release of numerous inflammatory cytokines, thereby preventing the cascade of immune and inflammatory signals.

In an embodiment, a calcineurin inhibitor such as cyclosporin A, voclosporin, ascomycin, tacrolimus, pimecrolimus, an analog thereof, or a pharmaceutically acceptable salt thereof is utilized in an aqueous nonirritating mixed nanomicellar formulation of the present disclosure. In an embodiment, the calcineurin inhibitor is voclosporin.

mTOR Inhibitors

Another class of compounds that exhibit this general therapeutic profile are the mTOR inhibitors. MTOR inhibitors target a molecular target known as "mammalian target of rapamycin" (mTOR). A prototypical compound of this class is sirolimus.

Sirolimus (rapamycin, Rapamune®, oral, Wyeth Pharmaceuticals, Inc.) is a microbial product isolated from the actinomycete *Streptomyces hygroscopicus*. Sirolimus was initially discovered as an antifungal agent in the 1970's, but because of its immunosuppressive effects, was not developed for use as an antibiotic. Structural similarities with tacrolimus eventually led researchers to investigate immunosuppressive properties of sirolimus in experimental organ transplantation. (Gummert et al., 1999). Sirolimus binds to an immunophilin (FK-binding protein 12, FKBP12), but the complex inhibits the mammalian target of rapamycin (mTOR) pathway through directly binding the mTOR Complex1 (mTORC1). Sirolimus inhibits the response to interleukin-2 (IL-2) and thereby blocks activation of T- and B-cells. By contrast, tacrolimus and cyclosporine inhibit the production of IL-2. Sirolimus (rapamycin) is disclosed in a method of treating ocular inflammation in Kulkarni in U.S. Pat. No. 5,387,589. Formulations for ocular treatment comprising sirolimus are disclosed in Dor et al., WO 2006/086744.

In an embodiment, an immunosuppressive mTOR inhibitor, such as sirolimus (rapamycin), temsirolimus, everolimus, an analog thereof, or a pharmaceutically acceptable salt thereof is utilized in an aqueous nonirritating mixed nanomicellar formulation of the present disclosure.

Corticosteroids

Corticosteroids are a family of compounds that include the adrenal steroid hormone cortisol (hydrocortisone) and related synthetic drugs, including, but not limited to, prednisolone, methylprednisolone, prednisone, triamcinolone, betamethasone, budesonide, and dexamethasone. Adrenal corticosteroids are hormones extracted from the adrenal cortex or a synthetic substance similar in chemical structure and biologic activity to such a hormone. Corticosteroids have similar mechanisms of action: they bind to specific corticosteroid binding proteins in the cytoplasm. These complexes are then transported into the nucleus where they bind to discrete portions of the cell's DNA. Corticosteroids are generally grouped into four classes, based on chemical structure.

Prednisolone is a corticosteroid drug with predominantly glucocorticoid and low mineralocorticoid activity, making it useful for the treatment of a wide range of inflammatory and auto-immune conditions including, but not limited to, asthma, uveitis, rheumatoid arthritis, ulcerative colitis and Crohn's disease, Bell's palsy, multiple sclerosis, cluster headaches, and Systemic Lupus Erythematosus. Prednisolone acetate ophthalmic suspension is an adrenocortical steroid product prepared as a sterile ophthalmic suspension, used to reduce swelling, redness, itching, and allergic reactions affecting the eye.

Methylprednisolone is a synthetic glucocorticoid drug. Like most adrenocortical steroids, methylprednisolone is typically used for its anti-inflammatory effects. The list of medical conditions for which methlyprednisolone is prescribed is rather long, and is similar to other corticosteroids such as prednisolone.

Prednisone is a synthetic corticosteroid drug that is usually taken orally but can be delivered by intramuscular injection and can be used for a number of different conditions. It has a mainly glucocorticoid effect. Prednisone is a prodrug that is converted by the liver into prednisolone, which is the active drug and also a steroid.

Triamcinolone is a synthetic corticosteroid given orally, by injection, inhalation, or as a topical ointment or cream.

Hydrocortisone is a steroid hormone produced by the adrenal cortex. Hydrocortisone is commonly used for the short-term treatment of inflammation in the eye (due to allergy, injury or infection) or ear (due to eczema).

Betamethasone is a moderately potent glucocorticoid steroid with anti-inflammatory and immunosuppressive properties. Betamethasone is applied as a topical cream, ointment, foam, lotion or gel to treat itching (e.g. from eczema).

Dexamethasone is a potent synthetic corticosteroid. It has been demonstrated by animal and human studies based on an oral application to possess approximately six to seven times the potency of prednisolone and at least 30 times the potency of cortisone. The potency of this compound is accomplished by the addition of a methyl radical and a fluorine atom to the prednisolone radical. MAXIDEX® 0.1% (dexamethasone ophthalmic suspension) is an adrenocortical steroid prepared as a sterile topical ophthalmic suspension.

In an embodiment, corticosteroids such as prednisolone, methylprednisolone, prednisone, triamcinolone, hydrocortisone, betamethasone and dexamethasone are utilized in an aqueous nonirritating mixed nanomicellar formulation of the present disclosure. In an embodiment, the corticosteroid is dexamethasone.

In an embodiment, a mixed nanomicellar formulation of the present disclosure includes two non-ionic surfactants. In an embodiment, a mixed nanomicellar formulation of the present disclosure includes a first non-ionic surfactant with an HLB index greater than about 10, and a second non-ionic surfactant with an HLB index of greater than about 13. In an embodiment, the first non-ionic surfactant having a HLB greater than about 10 is selected from various chemical derivatives of vitamin E with ester and ether linkages of various chemical moieties to polyethylene glycol of various lengths. Particularly preferred are vitamin E tocopherol polyethylene glycol succinate (TPGS) derivatives with PEG molecular weights between about 500 and 6000 Da. In an embodiment, the vitamin E polymeric derivative with an HLB index greater than about 10 is vitamin E tocopherol polyethylene glycol 1000 succinate (Vitamin E TPGS, tocophersolan). In an embodiment, the Vitamin E TPGS contributes to the solubilization of the water-insoluble drug and may reduce ocular discomfort in aqueous conditions. In an embodiment, the vitamin E TPGS is present in from about 0.01% w/v to about 20% w/v of the composition. In an embodiment, the vitamin E TPGS is present in from about 1.0% w/v to about 7.0% w/v of the composition. It will be understood that throughout the specification the term weight percent (wt %) refers to mass per unit volume, unless otherwise specified.

Vitamin E Tocopherol Polyethylene Glycol 1000 Succinate (Vitamin E TPGS, tocopherlosan, MW, approximately 1,513 g/mol, Eastman Chemical Co., Kingsport, Tenn) is an amphipathic excipient which is a water soluble derivative of natural-source vitamin E. Vitamin E TPGS, or PEGylated vitamin E, is a vitamin E derivative in which polyethylene glycol subunits are attached by a succinic acid diester at the ring hydroxyl of the vitamin E molecule. Vitamin E TPGS is an amphipathic non-ionic surfactant with an HLB index of about 13. Various chemical derivatives of vitamin E TPGS including ester and ether linkages of various chemical moieties are included within the definition of vitamin E TPGS. In addition to serving as a source of water-soluble vitamin E, vitamin E TPGS has been suggested for use as an emulsifier, solubilizer, absorption enhancer, an a vehicle for lipid-soluble drug delivery formulations. Vitamin E TPGS is a component in an FDA approved product, Agenerse® (Amprenavir, an antiviral HIV protease inhibitor) of GlaxoSmithKline Pharmaceuticals.

In an embodiment, the second non-ionic surfactant having a HLB greater than about 13 is an amphipathic polyethylene glycol (PEG)-alkyl ether surfactant or polyethylene glycol (PEG)-alkyl aryl ether surfactant. In one aspect, this surfactant is selected from a PEG 5-100 octyl phenyl ether which has an HLB greater than about 13. In this aspect, the PEG octylphenyl compound is selected from octoxynol-9, octoxynol-10, octoxynol-11, octoxynol-12, octoxynol-13, octoxynol-16, octoxynol-20, octoxynol-25, octoxynol-30, octoxynol-33, octoxynol-40, octoxynol-70. In a specific aspect, the PEG-alkyl phenyl ether surfactant is octoxynol-40. In an embodiment, the octoxynol-40 contributes to the reduction of ocular discomfort, and to the formation of a stable, mixed micellar formulation that is optically clear. In another aspect, the surfactant with an HLB greater than about 10 is selected from a PEG-5-100 nonyl phenyl ether; tyloxapol (ethoxylated p-tert-octylphenol formaldehyde polymer), a PEG-fatty acid monoester surfactant, a PEG-glycerol fatty acid ester, and a PEG-sorbiton fatty acid ester. PEG-Fatty acid monoester surfactants include, but are not limited to, PEG-15 oleate, PEG-20 laurate, PEG-20 oleate, PEG-20 stearate, PEG-32 laurate, PEG-32 oleate, PEG-32 stearate, PEG-40 laurate, PEG-40 oleate, and PEG-40 stearate. PEG-Glycerol fatty acid esters include, but are not limited to, PEG-15 glyceryl laurate PEG-20 glyceryl laurate, PEG-30 glyceryl laurate, PEG-40 glyceryl laurate, and PEG-20 glyceryl stearate. PEG-sorbiton fatty acid esters include, but are not limited to, PEG-4 sorbiton monolaurate, PEG-4 sorbiton monostearate, PEG-5 sorbiton monooleate, PEG-20 sorbiton monolaurate, PEG-20 sorbiton monopalmitate, PEG-20 sorbiton monostearate, and PEG-20 sorbiton monooleate. In an embodiment, the second non-ionic surfactant with HLB greater than about 13 is octoxynol-40. Octoxynol-40 is used as a surfactant in a marketed formulation (Acular®, and Acular LS® of Allergan, Inc., CA). Octoxynol-40 (IGEPAL CA-897) has an HLB index of about 18. In an embodiment, the octoxynol-40 is present in from about 0.001% w/v to about 10% w/v of the composition. In an embodiment, the octoxynol-40 is present in from about 0.01% w/v to about 5.0% w/v of the composition.

In an embodiment, a formulation of the present disclosure comprising a water-insoluble (i.e., hydrophobic) drug can be topically applied to an eye in a method to treat a back-of-the-eye ocular condition. As will be shown in the Examples that follow, it has been found that after topical administration of a formulation of the present disclosure, the water-insoluble drug is able to reach the back of the eye, thus providing a treatment for back-of-the-eye ocular conditions. In an embodiment, the water-insoluble drug is present in the formulation at concentrations from about 0.01% w/v to about 10% w/v, preferably from about 0.1% w/v to about 3.0% w/v. In an embodiment, the water-insoluble drug is voclosporin, and the voclosporin is present in the formulation at a concentration from about 0.02% w/v to about 0.5% w/v. In an embodiment, the water-insoluble drug is dexamethasone, and the dexamethasone is present in the formulation at a concentration from about 0.1% w/v to about 1.0% w/v. In an embodiment, Vitamin E TPGS is present in the formulation at concentrations from about 0.001% w/v to about 20% w/v, from about 0.1% w/v to about 5% w/v. In an embodiment, Octoxynol-40 or its homolog mixtures are present in the formulation at concentrations from about 0.001% w/v to about 10% w/v, preferably from about 0.01% w/v to about 3.0% w/v. Preferably, the total amount of surfactants in a formulation of the presently disclosed embodiments is about 30 percent or less of the total formulation with the remaining major component being water.

In an embodiment, a formulation of the present disclosure comprises about 0.2% w/v of voclosporin, about 2.5% w/v of vitamin E TPGS, and about 2.0% w/v octoxynol-40. In an embodiment, a formulation of the present disclosure comprises about 0.5% w/v of voclosporin, about 3.5% w/v of vitamin E TPGS, and about 2.0% w/v octoxynol-40. In an embodiment, a formulation of the present disclosure comprises voclosporin at about 2.0% w/v. In an embodiment, a formulation of the present disclosure comprises about 0.1% w/v of dexamethasone, about 4.5% w/v of vitamin E TPGS, and about 2.0% w/v octoxynol-40. In an embodiment, a formulation of the present disclosure comprises about 0.2% w/v of rapamycin, about 4.5% w/v of vitamin E TPGS, and about 2.0% w/v octoxynol-40.

It should be understood that the formulations of the present disclosure can also comprise other components such as, but not limited to, buffers, lubricating agents, tonicity agents, anti-infective agents, antibacterial agents, antioxidants, bioadhesive polymers, viscosity enhancing agents, wetting agents, and preservatives. In any of the mixed formulations of the present disclosure for topical administration to the eye, the mixtures are preferably formulated at about pH 5 to about pH 8. This pH range may be achieved by the addition of buffers to the mixtures as described in the examples. In an embodiment, the pH range in the mixtures in a formulation is about pH 6.6 to about pH 7.0. It should be appreciated that the formulations of the present disclosure can be buffered by any common buffer system such as phosphate, borate, acetate, citrate, carbonate and borate-polyol complexes, with the pH and osmolality adjusted in accordance with well-known techniques to proper physiological values. The formulations of the presently disclosed embodiments are stable in buffered aqueous solution. That is, there is no adverse interaction between the buffer and any other component that would cause the compositions to be unstable.

Tonicity agents include, for example, mannitol, dextrose, sodium chloride, xylitol and glycerol. These tonicity agents can be used to adjust the osmolality of the compositions. In an embodiment, the osmolality of a formulation of the present disclosure is adjusted to be in the range of about 75 to about 350 mOsm/kg.

In an embodiment, a formulation of the present disclosure further comprises one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight. Bioadhesion systems have been used in dentistry, orthopedics, opthalmology, and in surgical applications. However, there has recently emerged significant interest in the use of bioadhesive materials in other areas such as soft tissue-based artificial replacements, and controlled release systems for local release of bioactive agents. Such applications include systems for release of drugs in the buccal or nasal cavity, and for intestinal or rectal administration.

In an embodiment, bioadhesive polymers are optionally incorporated in the formulation to enhance the viscosity and thereby to increase residence time in the eye. Bioadhesive polymers of the present disclosure include, for example, carboxylic polymers like Carbopol® (carbomers), Noveon® (polycarbophils), etc.; cellulose derivatives including alkyl and hydroxyalkyl cellulose like methylcellulose, hydroxypropylcellulose, carboxymethylcellulose, etc.; gums like locust beam, xanthan, agarose, karaya, guar, etc.; and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the formulation from about 0.01 wt % to about 10 wt %/volume; preferably 0.1 to about 5 wt %/volume. In an embodiment, the mixed nanomicellar formulation optionally further comprises hydrophilic polymer excipients selected from, for example, PVP-K-30, PVP-K-90, HPMC, HEC, and polycarbophil. In an embodiment, the polymer excipient is selected from PVP-K-90, PVP-K-30 or HPMC. In an embodiment, the polymer excipient is selected from PVP-K-90 or PVP-K-30.

In an embodiment, if a preservative is desired, the formulations may optionally be preserved with any well-known system such as benzyl alcohol with/without EDTA, benzalkonium chloride, chlorhexidine, Cosmocil® CQ, or Dowicil® 200.

Pharmaceutically acceptable packaging materials for the formulations can include, but are not limited to polypropylene, polystyrene, low density polyethylene (LDPE), high density polyethylene (HDPE), polycarbonate, polyvinylidine chloride, and other materials known to those skilled in the art. In an embodiment, the formulations are packaged aseptically employing blow-fill-seal technology. Blow-fill-seal (BFS) describes an aseptic filling process in which hollow containers are blow molded, filled with sterile product, and sealed, all in one continuous machine cycle. The technology is an alternative to conventional aseptic filling and capping operations, often providing cost savings through high output and process efficiency.

In an embodiment, the formulations disclosed herein are filled to single-use bottles, packets, LDPE BFS vials, ampoules, LDPE BFS containers, or HDPE BFS containers.

In an embodiment, multiple doses can be supplied as a plurality of single-use packages. In an embodiment, the formulations are conveniently packaged in a bottle, container or device that allows for metered application, including containers equipped with a dropper for topical ophthalmic application.

While the precise regimen is left to the discretion of the clinician, it is recommended that the formulations of the presently disclosed embodiments be topically applied by placing one to two drops, or more, in each eye 1 to 4 times daily. For example, the formulation may be applied 1, 2, 3, 4 or 8 times a day, or more. In an embodiment, a formulation of the present disclosure is topically applied by placing one to two drops in each eye once or twice daily.

In an embodiment, a formulation of the present disclosure is topically applied to an eye of a patient, transported into the eye, and releases a drug at a posterior portion of the eye with negligible drug accumulation in the middle portion of the eye. In an embodiment, negligible drug accumulation in the middle portion of the eye refers to negligible drug accumulation in at least one of the aqueous humor, lens, and vitreous humor. It is believed that the formulations of the present disclosure can significantly reduce side effects associated with current therapy to treat back-of-the-eye conditions. Adverse side effects of current corticosteroid therapy includes, but are not limited to, cataracts and ocular hypertension. These side effects often cause lowering therapeutic efficacy and discontinuation of therapy.

In an embodiment, a formulation of the present disclosure can be used as a topically applied drug delivery platform for delivery of a hydrophobic, water-insoluble drug to the back of the eye. In an embodiment, a formulation of the present disclosure is applied topically to an eye. In an embodiment, a formulation of the present disclosure is used to treat, reduce, prevent, ameliorate and/or alleviate ocular conditions in a patient or subject. In an embodiment, a formulation of the present disclosure is used to treat, reduce, prevent, ameliorate and/or alleviate a back-of-eye disease. Examples of "back-of-eye" disease include, among others, macular edema such as angiographic cystoid macular edema; retinal ischemia and choroidal neovascularization; macular degeneration; retinal diseases (e.g., diabetic retinopathy, diabetic retinal edema, retinal detachment); inflammatory diseases such as uveitis (including panuveitis) or choroiditis (including multifocal choroiditis) of unknown cause (idiopathic) or associated with a systemic (e.g., autoimmune) disease; episcleritis or scleritis; Birdshot retinochoroidopathy; vascular diseases (retinal ischemia, retinal vasculitis, choroidal vascular insufficiency, choroidal thrombosis); neovascularization of the optic nerve; and optic neuritis.

In an embodiment, an aqueous ophthalmic solution includes nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v. In an embodiment, the aqueous ophthalmic solution has a pH of 6.6 to 7.0.

In an embodiment, an eye drop formulation includes a corticosteroid at a concentration ranging from about 0.01% w/v to about 1.00% w/v; vitamin E TPGS at a concentration ranging from about 3.0% w/v to about 5.0% w/v; and octoxynol-40 at a concentration ranging from about 1.0% w/v to about 3.0% w/v, wherein the corticosteroid is solubilized through entrapment in a mixed micellar hydrophobic core of the vitamin E TPGS and the octoxynol-40. In an embodiment, after administration of a single dose of the eye drop formulation to a rabbit, dexamethasone tissue levels in posterior retina-choroid are equivalent to concentrations of at least 30 ng/g.

In an embodiment, a kit includes a unit dose of an aqueous ophthalmic solution comprising nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v, wherein the unit dose is contained within a vial prepared from a pharmaceutically acceptable packaging material. In an embodiment, the unit dose is about 50 µL.

A method of preparing nanomicelles of the present disclosure includes mixing a corticosteroid with a first surfactant having an HLB index greater than about 10 and a second surfactant having an HLB index of greater than about 13 in a solvent to form a solvent solution; evaporating the solvent solution to form a near-solid matter; hydrating the near-solid matter with an aqueous solution; and dissolving the near-solid matter to produce the nanomicelles, wherein the nanomicelles are optically clear. In an embodiment, the corticosteroid is selected from one of a prednisolone, methylprednisolone, prednisone, triamcinolone, hydrocortisone, betamethasone, dexamethasone, analog thereof or a combination thereof. In an embodiment, the corticosteroid is dexamethasone.

A method for treating, reducing, ameliorating, or alleviating an ocular condition in a subject includes providing an aqueous ophthalmic solution that includes nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v; and administering to the subject an amount of the aqueous ophthalmic solution at a frequency sufficient to treat, reduce, ameliorate, or alleviate the ocular condition. In an embodiment, the ocular condition is a back-of-the-eye condition or disorder. In an embodiment, the corticosteroid is selected from one of a prednisolone, methylprednisolone, prednisone, triamcinolone, hydrocortisone, betamethasone, dexamethasone, analog thereof or a combination thereof. In an embodiment, the corticosteroid is dexamethasone.

A method for treating, reducing, ameliorating, or alleviating an ocular condition in a subject includes providing an aqueous ophthalmic solution that includes nanomicelles in a physiologically acceptable buffer, having a pH of 5.0 to 8.0, wherein a corticosteroid at a concentration from about 0.01% w/v to about 1.00% w/v is solubilized through entrapment in a mixed micellar hydrophobic core with a corona composed of hydrophilic chains extending from the hydrophobic core, wherein the nanomicelles comprise vitamin E TPGS at a concentration ranging from about 3.0% w/v to about 5.0% w/v stabilized with octoxynol-40 at a concentration ranging from about 1.0% w/v to about 3.0% w/v; and administering to the subject an amount of the aqueous ophthalmic solution at a frequency sufficient to treat, reduce, ameliorate, or alleviate the ocular condition. In an embodiment, the corticosteroid is selected from one of a prednisolone, methylprednisolone, prednisone, triamcinolone, hydrocortisone, betamethasone, dexamethasone, analog thereof or a combination thereof. In an embodiment, the corticosteroid is dexamethasone.

A method of treating a back-of-the-eye disease includes topically applying a formulation of the present disclosure to the eye, the formulation comprising an aqueous solution of corticosteroid-loaded nanomicelles; transporting the corticosteroid-loaded nanomicelles by passive diffusion through the aqueous channels/pores of the sclera; transporting the corticosteroid-loaded nanomicelles by endocytosis through the choroid to the basolateral side of the retinal pigment epithelium; discharging the corticosteroid from the nanomicelles into the retinal pigment epithelium; and treating the back-of-the-eye disease. In an embodiment, the corticosteroid is selected from one of a prednisolone, methylprednisolone, prednisone, triamcinolone, hydrocortisone, betamethasone, dexamethasone, analog thereof or a combination thereof. In an embodiment, the corticosteroid is dexamethasone.

The presently disclosed embodiments are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

In general, all reagents were commercially available and used without further purification unless indicated otherwise. Voclosporin was obtained from Isotechnika, Inc., Edmonton, Alberta, Canada. The stock obtained from Isotechnika was stored by Lux Biosciences at the New Jersey Center for Biomaterials at Rutgers University; Cyclosporin A was obtained from Xenos Bioresources, Inc., Santa Barbara, Calif.; Sirolimus and Tacrolimus were obtained from Haorui Pharma-Chem, Inc., NJ; Dexamethasone was obtained from Biomol, Plymouth, Pa. Vitamin E TPGS (NF Grade) was obtained from Eastman Chemical Company, IGEPAL CA-897 (Octoxynol-40) was obtained from Rhodia, Inc., Distilled Deionized Water was prepared in house at UMKC (University of Missouri, Kansas City) by use of EASY Pure UV Compact Ultra Pure Water System, (Barnstead, Iowa). Kollidon® 30 (PVP), and Kollidon® 90 F (Povidone K 90) were obtained from BASF. Hydroxyethyl Cellulose, 100 cps, and 5000 cps were obtained from Spectrum, Methocel®, HPMC was obtained from Colorcon, Noveon®, Polycarbophil was obtained from Lubrizol Advanced Materials.

Example 1

Preparation of Mixed Nanomicellar Formulations

Mixed nanomicellar formulations of the present disclosure having drug concentrations of 0.02 wt %, 0.2 wt %, 0.4 wt %, 0.5 wt %, and 1.0 wt % were fabricated as described below. Basic 2× drug formulations were made in the ratios shown in Table 1. In one protocol, for example, calcineurin inhibitor and vitamin E TPGS required for approximately 50 mL were calculated, weighed, then mixed in about 5 mL 95% ethanol, until a clear solution was obtained. The ethanolic solution was evaporated under vacuum to get a thin film near-solid matter. Deionized water, approximately 25 mL, was mixed with octoxynol-40 and the solution was added to the thin film near-solid matter and sonicated for approximately 20 minutes to ensure complete formation of mixed micelles. The prepared 2× drug formulations were stored at room temperature. Alternatively, amounts of drug, vitamin E TPGS and octoxynol-40 required for approximately 50 mL were calculated, weighed, then mixed in about 5 mL 95% ethanol, and evaporated under vacuum to form a thin film near-solid matter. The thin film near-solid matter was then dissolved in approximately 25 mL deionized water and sonicated or mixed by rotary motion in a rotary evaporator for approximately 20 minutes to ensure complete formation of mixed micelles. The prepared 2× formulations were stored at room temperature.

TABLE 1

| Label/Ingredients | 1 | 2 | 3 |
|---|---|---|---|
| Drug | 0.4 | 0.8 | 1.0 |
| Vitamin E TPGS | 4.0 | 6.0 | 7.0 |
| Octoxynol-40 | 1.0 | 1.0 | 1.0 |

Basic 2× Formulations shown in Table 1 were prepared as described in the alternative protocol described in Example 1. Basic formulations were prepared where the calcineurin inhibitor or mTOR inhibitor was voclosporin, cyclosporin A, sirolimus or tacrolimus. In one preparation for 50 mL of formulation: a buffer mixture was prepared by dissolving amounts of components shown in Table 2 in 25 mL of deionized water to prepare a 2× buffer. The 2× buffer mixture was prepared both with and without (N/A) added preservatives.

TABLE 2

| Components | Amount for 50 mL | Amount for 50 mL | Amount for 50 mL | Amount for 50 mL |
|---|---|---|---|---|
| Sodium Phosphate, Dibasic | 0.4048 g | 0.4048 g | 0.4048 g | 0.4048 g |
| Sodium Phosphate, Monobasic | 0.4645 g | 0.4645 g | 0.4645 g | 0.4645 g |
| EDTA | 10 mg | N/A | 10 mg | N/A |
| Benzalkonium chloride | 10 mg | N/A | N/A | 10 mg |

The required amount of polymer excipient shown in Table 3A was dispersed in 2.5 mL 2× buffer mixture and gently vortexed to get a clear solution. The basic 2× formulation was added in equal volume and mixed to get uniform solution. The pH of the solution was adjusted with NaOH or HCl to a target of about pH 6.8. The osmolality of the solution was adjusted with NaCl to be in the range of about 280-300 mOsmol/kg. The formulation was sterilized by a nylon membrane filter (0.22 μm) and then stored at room temperature until use.

TABLE 3A

| Ingredients | 1 | 2 | 3 | 4 | 5 | 6 |
|---|---|---|---|---|---|---|
| Basic Formulation (2X) | 2.5 mL | 2.5 mL | 2.5 mL | 2.5 mL | 2.5 mL | 2.5 mL |
| Buffer Mixture (2X) | | 2.5 mL | 2.5 mL | 2.5 mL | 2.5 mL | 2.5 mL |
| PVP-K-30 (1.8%) | | 90 mg | | | | |
| PVP-K-90 (1.2%) | | | 60 mg | | | |
| HPMC (0.5%) | | | | 25 mg | | |
| HEC (0.5%) | | | | | 25 mg | |
| Polycarbophil (0.5%) | | | | | | 25 mg |
| Water | 2.5 mL | | | | | |
| Total Approx. Vol. | 5 mL | 5 mL | 5 mL | 5 mL | 5 mL | 5 mL |

In an alternative procedure for the preparation of 100 mL formulations, the basic 2× formulations shown in Table 1 were prepared using voclosporin ("VCS"). In order to make formulations at VCS concentrations of 0.2 wt %/volume, 0.4 wt %/volume and 0.5 wt %/volume, appropriate amounts of drug, vitamin E TPGS and octoxynol-40 required for 100 mL were calculated, weighed, then mixed in 10 mL 95% ethanol, and evaporated under vacuum for approximately 12 hours to form a thin film near-solid matter. The thin film near-solid matter was then dissolved in 50 mL deionized water and sonicated, or mixed by rotary motion in a rotary evaporator, for approximately 20 minutes to ensure complete formation of mixed micelles; then stored at room temperature. The required amount of polymer excipient shown in Tables 3B and 3C was dispersed in 40 mL deionized water and stirred to get a clear polymer solution. The other components shown in Tables 3B and 3C were added to the 50 mL basic 2× formulation and stirred well to get clear buffered solution. The clear buffered solution was slowly transferred into the clear polymer solution and mixed well. The pH of the solution was adjusted with NaOH or HCl to a target of about pH 6.8. The osmolality of the solution was maintained in the range of 280-300 mOsmol/kg. The volume was brought up to 100 mL with water. The formulation was sterilized by a nylon membrane filter (0.22 μm) and then stored at room temperature until use.

TABLE 3B

| Ingredients | 1 | 2 | 3 | 4 | 5 | 6 |
|---|---|---|---|---|---|---|
| Basic Formulation (2X) | 50 mL | 50 mL | 50 mL | 50 mL | 50 mL | 50 mL |
| Povidone-K-30 | | 1.8 g | | | | |
| Povidone-K-90 | | | 1.2 g | | | |
| Hydroxy propyl methyl cellulose | | | | 0.5 g | | |
| Hydroxyethyl cellulose | | | | | 0.5 g | |
| Polycarbophil | | | | | | 0.9 g |
| Sodium phosphate, dibasic heptahydrate | 0.81 g | 0.81 g | 0.81 g | 0.81 g | 0.81 g | 0.81 g |
| Sodium phosphate, monobasic | 0.93 g | 0.93 g | 0.93 g | 0.93 g | 0.93 g | 0.93 g |
| Sodium chloride | 0.2 g | 0.2 g | 0.2 g | 0.2 g | 0.2 g | 0.2 g |
| Water up to | 100 mL | 100 mL | 100 mL | 100 mL | 100 mL | 100 mL |

TABLE 3C

| Ingredients | Label 1 | Label 2 | Label 3 | Label 4 | Label 5 | Label 6 |
|---|---|---|---|---|---|---|
| Basic Formulation (2X) | 50 mL | 50 mL | 50 mL | 50 mL | 50 mL | 50 mL |
| Povidone-K-30 | | 1.8 g | | | | |
| Povidone-K-90 | | | 1.2 g | | | |
| Hydroxy propyl methyl cellulose | | | | 0.5 g | | |
| Hydroxyethyl cellulose | | | | | 0.5 g | |
| Polycarbophil | | | | | | 0.9 g |
| Sodium phosphate, dibasic heptahydrate | 0.81 g | 0.81 g | 0.81 g | 0.81 g | 0.81 g | 0.81 g |
| Sodium phosphate, monobasic | 0.93 g | 0.93 g | 0.93 g | 0.93 g | 0.93 g | 0.93 g |
| Sodium chloride | 0.2 g | 0.2 g | 0.2 g | 0.2 g | 0.2 g | 0.2 g |
| Benzylkonium chloride | 0.02 g | 0.02 g | 0.02 g | 0.02 g | 0.02 g | 0.02 g |
| EDTA | 0.02 g | 0.02 g | 0.02 g | 0.02 g | 0.02 g | 0.02 g |
| Water up to | 100 mL | 100 mL | 100 mL | 100 mL | 100 mL | 100 mL |

In an embodiment, a nanomicellar formulation of the present disclosure having a VCS concentration of 0.2% w/v, is an ophthalmic solution having the composition found in Table 3D:

TABLE 3D

| Ingredient | Amount |
|---|---|
| Voclosporin | 0.2 g |
| Vitamin E TPGS | 2.0 g |
| Octoxynol-40 | 2.0 g |
| PVP-K-90 | 1.2 g |
| Sodium Phosphate, Dibasic | 0.81 g |
| Sodium Phosphate, Monobasic | 0.93 g |
| Sodium Chloride | 0.2 g |
| Water up to | 100 mL |

In an embodiment, a nanomicellar formulation of the present disclosure having a Cyclosporin A ("CsA") concentrations of 0.05% w/v, is an ophthalmic solution having the composition found in Table 4:

TABLE 4

| Label/Ingredients | wt %/vol |
|---|---|
| Drug (CsA) | 0.05 |
| Vitamin E TPGS | 3 |
| Octoxynol-40 | 0.02 |
| Hydroxy Ethyl Cellulose | 0.2 |
| Benzalkonium Chloride | 0.01 |

TABLE 4-continued

| Label/Ingredients | wt %/vol |
|---|---|
| EDTA | 0.01 |
| Sodium Chloride | 0.86 |
| Water up to | 100 |

The formulation shown in Table 4 was fabricated using a similar fashion as described in the alternative protocol in Example 1. The CsA formulation was adjusted to a pH of about 6.88 and osmolality was 320 mOsm/kg.

Example 2

Ocular Distribution and Pharmacokinetics of $^{14}$C-Voclosporin after Topical Administration of a 0.2 wt %/vol. Voclosporin Nanomicellar Formulation (LX214)

NZW rabbits (30 females/8 males) were used in a single dose (SD) and 7-day repeat dose (RD) study (Table 5A). DB rabbits (16 females) were used in a single dose study (Table 5B). Animals were either not treated (controls) or given a single or a daily topical ocular dose for 7 days (35 μA of 0.2% $^{14}$C-LX214 solution to one or both eyes). Blood and ocular tissue radioactivity levels were assessed at designated time points via combustion followed by liquid scintillation counting. Voclosporin concentrations were also measured in blood using a validated liquid chromatography coupled with atmospheric pressure ionization mass spectrometry (LC-API/MS/MS) method.

TABLE 5A

| Group ID | No. of Animals/group | $^{14}$C-Dose Administration[a] | Matrices Collected | Sample Collection Time (Time of euthanasia) |
|---|---|---|---|---|
| 1[b] | 2 ♀ | None | Tear, Blood, Ocular Tissues/Fluids | Pre-dose |
| | 2 ♂ | | | |
| 2[c] | 12 ♀ | 35 μL/eye, once, Ocular (bilateral) | Tear, Blood, Ocular Tissues/Fluids (SD group) | ♀: 0.5, 1, 2, 4, 8, and 24 hr ♂: 1, 4, and 24 hr After the dose administration (2 animals/time point) |
| | 6 ♂ | | | |
| 3 | 2 ♀ | 35 μL/eye, once, Ocular (unilateral) | Tear, Blood, Ocular Tissues/Fluids | 1 hr after the dose administration |

TABLE 5A-continued

| Group ID | No. of Animals/group | $^{14}$C-Dose Administration[a] | Matrices Collected | Sample Collection Time (Time of euthanasia) |
|---|---|---|---|---|
| 4[d] | 2 ♀ | 35 µL/eye, once daily, bilateral for 6 days | Tear, Blood Ocular Tissues/Fluids | Just prior to 7$^{th}$ dose administration in the next group |
| 5[e] | 12 ♀ | 35 µL/eye, once daily, bilateral for 7 days | Tear, Blood Ocular Tissues/Fluids (RD group) | 0.5, 1, 2, 4, 8, and 24 hr after the last dose administration (2 animals/time point) |

[a]The topical dose formulation contained 0.2% voclosporin. The target dose was ~3 µCi/35 µL and 70 ng voclosporin.
[b]Used as predose concentration for Treatment Group 2 (SD group).
[c]Used for pharmacokinetic assessment (SD group).
[d]Used as predose concentration for Treatment Group 5 (RD group).
[e]Used for pharmacokinetic assessment (MD group).

TABLE 5B

| Group ID | No. of Animals/group | $^{14}$C-Dose Administration[a] | Matrices Collected | Sample Collection Time (Time of Euthanasia) |
|---|---|---|---|---|
| 1[b] | 2 ♀ | None | Tear, Blood, Ocular Tissues/Fluids | Pre-dose |
| 2[c] | 12 ♀ | 35 µL/eye, once, Ocular (bilateral) | Tear, Blood, Ocular Tissues/Fluids (SD group) | 0.5, 1, 2, 4, 8, and 24 hr after the dose administration (2 animals/time point) |
| 3 | 2 ♀ | 35 µL/eye, once, Ocular (unilateral) | Tear, Blood, Ocular Tissues/Fluids | 1 hr after dose administration |

[a]The topical dose formulation contained 0.2% voclosporin. The target dose was ~3 µCi/35 µL and 70 ng voclosporin/dose.
[b]Used as predose concentration for Treatment Group 2 (SD group).
[c]Used for pharmacokinetic assessment (SD group).

At each sampling point, a t-test was used to compare the tissue concentrations within or between the two strains of rabbits. SigmaStat® 3.5 (Systat, Inc., San Jose, Calif.) was used for the statistical analyses (p<0.05). Non-compartmental analysis was performed on the mean tissue $^{14}$C-LX214 concentration-time data. Pharmacokinetic analysis was performed using WinNonlin 5.2 (Pharsight, Corporation, Mountain View, Calif.). $C_{max}$ and $T_{max}$, and where calculable AUC and $t_{1/2}$, are reported.

Selected pharmacokinetic parameters ($C_{max}$, AUC, $T_{max}$, and $t_{1/2}$) for $^{14}$C-LX214-derived radioactivity following a single dose (SD) or repeat dose (RD) (once-a-day for 7 days), bilateral ocular administration are summarized in Tables 6 and 7 for NZW female and DB female rabbits, respectively. After a single dose, there was rapid penetration of drug (measured as radioactivity) into ocular tissues with the highest concentrations (>1 mg eq/g tissue) occurring in the eyelids, conjunctiva, cornea, nictitating membrane and tears, and the lowest concentrations (1-11 ng eq/g tissue) in the aqueous and vitreous humor, and the lens. The remaining ocular tissues achieved various levels (20-223 ng eq/g tissue) of voclosporin and/or related residue. Following repeat dosing of up to 7 days, there was no apparent change in $^{14}$C-LX214 $t_{1/2}$, suggesting minimal tissue accumulation (Table 6). In the posterior portions of the eye (for example, the choroid/retina and the optic nerve), the measured level at each time point was substantially higher than the presumed therapeutic concentration of 30 eq ng/g. However, no significant drug accumulation, in comparison with the tissue levels post single dose, was observed after repeat dosing for 7 days. High levels of drug are achievable with one topical application (single dose) of the formulation of the present disclosure. More particularly, high drug levels were maintained in ocular tissues for up to, and beyond, 24 hours post-administration, suggesting that QD (once-a-day) dosing is achievable using the compositions of the present disclosure. The concentration of drug is high in tissues in the front of the eye (cornea, conjunctiva, sclera) and at the back of the eye (retina, optic nerve) but minimal in the middle of the eye (aqueous and vitreous humor), suggesting transport of the drug by a mechanism other than passively through the eye. The high drug levels achieved at the back of the eye make topical administration of the compositions of the present disclosure feasible for the treatment of diseases of the back-of-the-eye (e.g., retinal, diseases involving optic nerve such as glaucoma). Various water-insoluble drugs can be used with the compositions of the present disclosure, including, but not limited to, calcineurin, MTOR inhibitors, and corticosteroids. High levels, especially in back-of-the-eye tissues such as choroid/retina and optic nerve, have been shown with the formulations of the present disclosure.

TABLE 6

| Ocular Tissue(s)/Fluids & Blood | $C_{max}$ (ng eq./g) | | | AUC (hr * ng eq./g) | | | $T_{max}$ (hr) | | $t_{1/2}$ (hr) | |
|---|---|---|---|---|---|---|---|---|---|---|
| | SD | RD | Ratio | SD | RD | Ratio | SD | RD | SD | RD |
| Aqueous Humor | 6 | 13 | 2.3 | 45 | 96 | 2.1 | 0.5 | 0.5 | — | 14 |
| Choroid/Retina | 48 | 76 | 1.6 | 472 | 897 | 1.9 | 1.0 | 2.0 | 23 | — |
| Cornea | 1203 | 3382 | 2.8 | 23166 | 54624 | 2.4 | 8.0 | 0.5 | — | — |
| Iris/Ciliary Body | 20 | 119 | 5.8 | 382 | 1952 | 5.1 | 24.0 | 1.0 | — | — |
| Lacrimal Gland | 31 | 120 | 3.9 | 416 | 1109 | 2.7 | 2.0 | 4.0 | — | 6 |

TABLE 6-continued

| Ocular Tissue(s)/Fluids & Blood | $C_{max}$ (ng eq./g) | | | AUC (hr * ng eq./g) | | | $T_{max}$ (hr) | | $t_{1/2}$ (hr) | |
|---|---|---|---|---|---|---|---|---|---|---|
| | SD | RD | Ratio | SD | RD | Ratio | SD | RD | SD | RD |
| Lens | 4 | 26 | 6.7 | 47 | 356 | 7.5 | 24.0 | 0.5 | — | — |
| Lower Bulbar Conjunctiva | 1810 | 2929 | 1.6 | 12029 | 16585 | 1.4 | 0.5 | 0.5 | 10 | 7 |
| Lower Eyelid | 20814 | 41635 | 2.0 | 207630 | 358791 | 1.7 | 1.0 | 0.5 | — | — |
| Nictitating Membrane | 1716 | 2468 | 1.4 | 12135 | 15964 | 1.3 | 0.5 | 0.5 | 7 | 8 |
| Optic Nerve | 83 | 164 | 2.0 | 569 | 1805 | 3.2 | 0.5 | 0.5 | — | 16 |
| Sclera | 223 | 367 | 1.6 | 2646 | 3825 | 1.4 | 0.5 | 0.5 | — | 16 |
| Submandibular Lymph Node | 74 | 120 | 1.6 | 893 | 1190 | 1.3 | 2.0 | 2.0 | — | — |
| Tear | 20246 | 30904 | 1.5 | 168259 | 230878 | 1.4 | 0.5 | 0.5 | — | 7 |
| Upper Bulbar Conjunctiva | 2235 | 3170 | 1.4 | 14782 | 19944 | 1.3 | 0.5 | 0.5 | 7 | 7 |
| Upper Eyelid | 9896 | 17500 | 1.8 | 114651 | 98656 | 0.9 | 1.0 | 0.5 | — | 4 |
| Vitreous Humor | 2 | 2 | 1 | 27 | 23 | 0.9 | 8.0 | 4.0 | — | — |
| Blood | BQL | BQL | NC | NC | NC | NC | NC | NC | NC | NC |

SD = Single dose; RD = Repeat Dose; Ratio = Repeat Dose/Single Dose.; — = Insufficient tissue concentrations to determine $t_{1/2}$; BQL = Below Quantifiable Limit (<0.1 ng/mL); NC = Not calculated.

TABLE 7

| Ocular Tissue(s)/Fluids & Blood | $C_{max}$ (ng eq./g) | $T_{max}$ (hr) | $t_{1/2}$ (hr) | AUC (hr * ng eq./g) |
|---|---|---|---|---|
| Aqueous Humor | 11 | 0.5 | — | 56 |
| Choroid/Retina | 49 | 1.0 | — | 92 |
| Cornea | 1519 | 8.0 | — | 27844 |
| Iris/Ciliary Body | 30 | 24.0 | — | 541 |
| Lacrimal Gland | 75 | 1.0 | — | 335 |
| Lens | 2 | 24.0 | — | 26 |
| Lower Bulbar Conjunctiva | 2080 | 1.0 | 15 | 13107 |
| Lower Eyelid | 69055 | 4.0 | — | 512473 |
| Nictitating Membrane | 2400 | 1.0 | 12 | 13091 |
| Optic Nerve | 192 | 1.0 | 16 | 1127 |
| Sclera | 220 | 1.0 | — | 3502 |
| Submandibular Lymph Node | 86 | 4.0 | — | 635 |
| Tear | 57476 | 1.0 | — | 262299 |
| Upper Bulbar Conjunctiva | 2491 | 1.0 | 14 | 14296 |
| Upper Eyelid | 8245 | 4.0 | — | 68063 |
| Vitreous Humor | 1 | 1.0 | — | 16 |
| Blood | BQL | NC | NC | NC |

Table 8 shows comparative $C_{max}$ of $^{14}C$-voclosporin derived radioactivity in NZW and DB rabbits after single topical ocular administration of $^{14}C$-voclosporin.

TABLE 8

| Ocular Tissue(s)/Fluids & Blood | New Zealand White (Study No. S08861) $C_{max}$ (ng eq./g) | Dutch Belted (Study No. S08862) $C_{max}$ (ng eq./g) |
|---|---|---|
| Aqueous humor | 6 | 11 |
| Choroid/Retina | 48 | 49 |
| Cornea | 1203 | 1519 |
| Iris/Ciliary Body | 20 | 30 |
| Lacrimal Gland | 31 | 75 |
| Lens | 4 | 2 |
| Lower Bulbar Conjunctiva | 1810 | 2080 |
| Lower Eyelid | 20814 | 69055 |
| Nictitating membrane | 1716 | 2400 |
| Optic Nerve | 83 | 192 |
| Sclera | 223 | 220 |
| Submandibular Lymph Node | 74 | 86 |
| Tear | 20246 | 57476 |
| Upper Bulbar Conjunctiva | 2235 | 2491 |
| Upper Eyelid | 9896 | 8245 |
| Vitreous Humor | 2 | 1 |
| Blood | BQL | BQL |

Example 3

Preparation of a Dexamethasone Mixed Nanomicellar Formulation

The aqueous solubility of corticosteroids, such as dexamethasone, is approximately 0.159 mg/mL. In this example, the solubility of the drug, dexamethesaon, was improved by about 6.2 fold (1 mg/mL). In an embodiment, in order to make a composition at a drug concentration (dexamethasone) of 0.1 wt %, the following protocol was employed. Drug basic formulation was made in the ratios shown in Table 9. In this protocol, dexamethasone, vitamin E TPGS and octoxynol-40 were calculated, weighed, then mixed in 6 mL 95% ethanol for a final 50 mL formulation, until a clear solution was obtained. The ethanolic solution was evaporated under vacuum to get a thin film near-solid matter. Deionized water, 25 mL, was added to the thin film near-solid matter and sonicated for approximately 20 min to ensure complete formation of mixed micelles. The prepared 2× formulation was stored at room temperature.

TABLE 9

| Label/Ingredients | Wt % |
|---|---|
| Drug | 0.1 |
| Vitamin E TPGS | 4.5 |
| Octoxynol-40 | 2.0 |

General Preparation of Composition:

Basic 2× formulation shown in Table 9 was prepared as described in the protocol basic formulation where the employed drug was the steroid dexamethasone. In the preparation of a 50 mL formulation: a buffer mixture was prepared by dissolving amounts of components shown in Table 10 in 25 mL of deionized water to prepare a 2× buffer.

TABLE 10

| Components | Amount for 50 mL final formulation |
|---|---|
| Sodium phosphate dibasic (0.81%) | 0.2025 g |
| Sodium phosphate monobasic (0.93%) | 0.2325 g |
| Sodium chloride (0.18%) | 0.045 g |

Polymer excipient (PVP-K-90, 1.2%, 0.3 g for 50 mL) was dispersed in 25 mL 2× buffer mixture and gently vortexed to get a clear solution. The basic 2× formulation was added in equal volume and mixed to get uniform solution. The pH of the solution was adjusted with NaOH or HCl to a target pH 6.8. The osmolality of the solution was adjusted with NaCl to be in the range of about 280-300 mOsmol/kg. The formulation was sterilized by a nylon membrane filter (0.22 µm) and then stored at 4° C. until use.

In an embodiment, a dexamethasone mixed nanomicellar formulation of the present disclosure include the components listed in Table 11:

TABLE 11

| Components (w/v %) | Weight (g) |
| --- | --- |
| Dexamethasone (0.1%) | 0.025 g |
| Vit. E TPGS (4.5%) | 1.125 g |
| Octoxynol-40 (2.0%) | 0.5 g |
| Sodium phosphate dibasic (0.81%) | 0.2025 g |
| Sodium phosphate monobasic (0.93%) | 0.2325 g |
| Sodium chloride (0.18%) | 0.045 g |
| PVP K-90 (1.2%) | 0.3 g |

Stability tests showed that after about 40 days in the refrigerator (~4° C.) the dexamethasone concentration in the composition remained about constant (samples were diluted 1000 times before analysis). The analysis of dexamethasone in the stability samples were analyzed using reverse phase high performance liquid chromatography. Mobile phase consisted of 40% acetonitrile: 60% water: 0.1% trifluoroacetic acid, pumped at a flow rate of 1 ml/min. Stationary phase consisted of a C18-column, 250×4.6 mm (Phenomenex, Torrance, Calif.). Particle size of the mixed micellar compositions comprising 0.1% dexamethasone showed micelle size of approximately 20 nm. The viscosity of 0.1% mixed micellar formulation was measured to be 2.79 centi poise. The optical clarity was assessed by measuring the absorbance of the formulation at 400 nm using UV-Visible spectrophotometer, (Model: Biomate-3, Thermo Spectronic, Waltham, Mass.), with water as blank. Formulation was clear, since the UV absorbance of the formulation containing the drug was similar to water (blank).

Example 4

Ocular Distribution and Pharmacokinetics of $^{14}$C-Dexamethasone after Topical Administration of a 0.1 wt %/vol. Dexamethasone Nanomicellar Formulation This study was carried out to assess the temporal distribution of a 0.1% wt %/vol. topical formulation of dexamethasone of the present disclosure after ocular application (single dose of 50 µL per eye) by determining concentration in ocular tissues, tears, and blood in male New Zealand White (NZW) rabbits.

Male NZW rabbits (n=4) weighing between 2.0 and 2.5 kilograms were used in a single dose (SD) study. Animals were anesthetized prior to the experiment by means of ketamine HCl (35 mg/kg) and xylazine (3.5 mg/kg) administered intramuscularly. Anesthesia was maintained throughout the experiment. Fifty microliters of 0.1% dexamethasone mixed micellar formulation (Vitamin E TPGS-4.5% and Octoxynol-40-2.0%) was instilled topically. After a period of 60 min, euthanasia was performed under deep anesthesia with an intravenous injection of sodium pentobarbital through the marginal ear vein. Following euthanasia, the eye ball was enucleated immediately (on an average within 150 seconds) and transferred to a beaker containing ice-cold phosphate buffer (pH 7.4). Repetitive washings were carried out in cold phosphate buffer to remove any drug adsorbed on to the surface. Aqueous humor was withdrawn by limbal paracentesis and then vitreous humor was aspirated using a 1 ml tuberculin syringe after making a tiny incision at sceral limbus junction. The enucleated eyeball was cut open and the following tissues were dissected: cornea, iris-ciliary body (ICB), lens, retina-choroid (RC) and sclera. After dissection, the tissues were dried with Kimwipes® and weighed. Protein content in the aqueous and vitreous humor was measured by the method of Bradford (Bio-Rad protein estimation kit, Hercules, Calif.). All tissue samples were stored at −80° C. before further analysis.

Tissues were homogenized in approximately 500 µl chilled (4° C.) phosphate buffer (pH 7.4) for about 4 min with a tissue homogenizer (Tissue Tearor, Model 985-370; Dremel Multipro, Racine, Wis.) in an ice bath, with the exception of sclera which required 1.5 ml of buffer. Two hundred microliters of aqueous humor (AH) and vitreous humor (VH) were used for analysis as such without further processing. Subsequently, 200 µl of the tissue homogenates (cornea, iris-ciliary body, lens, retina-choroid and sclera), aqueous humor and vitreous humor were used for further sample processing.

Dexamethasone was extracted from the ocular tissue homogenates using simple liquid-liquid extraction. Prednisolone was used as an internal standard (IS) in the quantitative LC-MS/MS assay for Dexamethasone. Twenty five microliters of IS at a concentration of 10 µg/ml was added to all the tissue homogenate samples and vortexed for 30 seconds. Five hundred microliters of t-butyl methyl ether was added to the samples and then vortexed vigorously for 1 min. Samples were then centrifuged at 10,000 rpm for 25 min at 4° C. The supernatant was then separated and evaporated using Speed-Vac® (SAVANT Instruments, Inc., Holbrook, N.Y.). The dry residues were dissolved in 100 µl of acetonitrile:water (70:30) containing 0.05% formic acid and then the sample was vortexed for 1 min. Calibration standards were prepared by spiking appropriate control tissues (tissues obtained from non-treated animals) with varying concentrations of dexamethasone. All standards and the samples were subjected to the same extraction procedure. All standards and samples were analyzed using LC-MS/MS.

The analysis of dexamethasone from the ocular tissue homogenates was performed using a triple quadrupole mass spectrometer with electrospray ionization (ESI) on a turbo ionspray source (API 2000; Applied Biosystems, Foster City, Calif., USA) coupled to a liquid chromatography system (Agilent HP1100, Agilent Technology Inc., Palo Alto, Calif., USA) and C18-column 50×4.6 mm (Phenomenex, Torrance, Calif.). The mobile phase consisted of 70% acetonitrile and 30% water with 0.1% formic acid and was pumped at a flow rate of 0.2 ml/min. The sample volume injected was 25 µl and the analysis time was 7 min. Multiple reaction monitoring (MRM) mode was utilized to detect the compound of interest. The limit of quantitation was found to be 2.7 ng/ml. Table 12 shows the concentration of dexamethasone achieved in ocular fluids and tissues following a single topical eye drop administration of 0.1% dexamethasone mixed nanomicellar formulation of the present disclosure.

TABLE 12

| Ocular Tissue(s)/Fluids & Blood | C ± SD (ng eq./g) |
|---|---|
| Choroid/Retina | 48.5 ± 23.1 |
| Cornea | 1050.7 ± 446.8 |
| Iris/Ciliary Body | 529.6 ± 309.1 |
| Aqueous humor | 344.0 ± 116.7 |
| Sclera | 103.9 ± 67.1 |
| Lens | Not Detectable |
| Vitreous humor | Not Detectable |

Reports indicate that the therapeutic concentration levels of dexamethasone required in the vitreous humor for the treatment of posterior uveitis is 0.01-4.0 µg/mL. It is believed that the disclosed nanomicellar formulations can significantly reduce the side effects associated with current therapy to treat back-of-the-eye conditions. For example, such adverse side effects of current steroid therapy include cataract and ocular hypertension. As a result dose limiting long term toxicities such as cataract and ocular hypertension or glaucoma can be reduced or completely avoided. These side effects often cause lowering therapeutic efficacy and discontinuation of therapy. Using a nanomicellar formulation of the present disclosure, a concentration of dexamethasone achieved in the retina-choroid (RC ~50 ng/g tissue) after a single eye drop administration (50 µL) falls in the therapeutic concentration range for the treatment of posterior segment diseases. It is believed that higher concentration levels might be achieved in RC following multiple dosing or by higher drug loading within the nanomicelles. Interestingly, the concentration of dexamethasone in lens and vitreous humor was below the detection limit (LOD=2.5 ng/mL). This interesting result suggests that upon topical administration, the nanomicelles permeate through the scleral aqueous channels/pores reaching the RPE transclerally (around the globe) and not intraocularly through the lens and vitreous humor. Though intravitreal injection/implant directly delivers the compounds to the posterior segment of the eye, their inherent potential side effects like increased intraocular pressure, hemorrhage, retinal detachment, cataract, endophthalmitis, lead to complications limiting long term therapy. Negligible concentration levels in lens and vitreous humor suggests that these side-effects could be greatly diminished or even eliminated using the newly developed mixed nanomicellar formulation.

Example 5

Preparation of a Rapamycin (Sirolimus) Mixed Nanomicellar Formulation

Rapamycin (sirolimus) is a USFDA approved mTOR inhibitor. It is a hydrophobic drug with a low aqueous solubility (2.6 µg/mL). In this example, the solubility of the drug, rapamycin, was improved by up to about 2000 fold (4 mg/mL).

Nanomixed micelle formulation of rapamycin (sirolimus) of approximately 25 nm was prepared by a solvent evaporation method. The preparation of formulation was divided into two steps: 1. Preparation of basic formulation and 2. rehydration. Briefly, 200 mg of rapamycin, 4.5 gm of Vit E TPGS and 2 gm of octoxynol-40 were dissolved in 10 mL of ethanol separately. All the three solutions were mixed together in a round bottom flask. The solution was mixed to get a homogenized solution. Solvent was evaporated by rotary evaporation to obtain a solid thin film. The residual ethanol in the formulation was removed under high vacuum overnight at room temperature. The resultant thin film was hydrated with 50 mL of double distilled water. The rehydrated formulation was subjected to sonication, for approximately 20 mins. The obtained rehydrated formulation was made up with phosphate buffer solution, pH 6.8, to 100 mL which was then filtrated through 0.2 µm nylon filter membrane to sterilize and remove any other foreign particulate matter.

Example 6

Ocular Distribution and Pharmacokinetics of $^{14}$C-Rapamycin after Topical Administration of a 0.2 wt %/vol. Rapamycin Nanomicellar Formulation For animal studies, 0.2% rapamycin formulations (2 mg/mL), which showed an 1000 fold increase in solubility, was used. The animal protocol for this experiment was approved by University of Missouri Kansas City Institutional Animal Care and Use committee (UMKC IACUC). NZW male rabbits weighing approximately 2.5 kg were obtained from Myrtle's Rabbitry (Thompson Station, Tenn.). Animals were acclimated for 24 hours in the UMKC animal facility. For treatment, N=3 animals were used. Animals were anesthetized prior to the experiment by means of ketamine HCl (35 mg/kg) and xylazine (3.5 mg/kg) administered intramuscularly. Anesthesia was maintained throughout the experiment. Fifty microliters of 0.2% rapamycin mixed nanomicellar formulation (Vit. E TPGS-4.5% and Octoxynol-40-2.0%) was instilled topically into conjuctival sac of left eye. One minute prior to the instillation of formulation, fifty microliters of buffer was instilled topically into the conjuctival sac of right eye as control treatment. After a period of 60 min, euthanasia was performed under deep anesthesia with an intravenous injection of sodium pentobarbital through the marginal ear vein.

Following euthanasia, the eye ball was enucleated immediately and transferred to a beaker containing ice-cold phosphate buffer (pH 7.4). Enucleated eye balls were washed twice in cold phosphate buffer to remove any drug adsorbed on to the surface. Aqueous humor (AH) was withdrawn by limbal paracentesis and then vitreous humor (VH) was aspirated using a 1 mL tuberculin syringe after making a tiny incision at sceral limbus junction. The enucleated eyeball was cut open and the following tissues were dissected: cornea, iris-ciliary body (ICB), lens, retina-choroid (RC) and sclera. After dissection, the tissues were dried with Kimwipes® and weighed. All tissues were homogenized using the following procedure described below and were stored at −80° C. Tissue homogenates were thawed. Protein content was determined on an aliquot and another aliquot of each homogenate was utilized for rapamycin content as described below.

Tissue Homogenization:

Four tissues (retina-choroid, lens, cornea and iris ciliary body) per animal were homogenized in 500 µL it chilled (4° C.) phosphate buffer (pH 7.4) for about 4 min with a tissue homogenizer (Tissue Tearor, Model 985-370; Dremel Multipro, Racine, Wis.) in an ice bath. Sclera required 2.0 mL of buffer for homogenization. Aqueous humor and vitreous humor did not require homogenization.

Protein Determination:

Protein content in the tissue extracts (cornea, lens, sclera, retina-choroid, iris ciliary bodies), aqueous and vitreous humor was measured by the method of Bradford (Bio-Rad protein estimation kit, Hercules, Calif.) following the manufacturers guidelines.

Extraction for Rapamycin Determination:

Two hundred μL of each tissue homogenate (cornea, iris-ciliary body, lens, retina-choroid and sclera), aqueous humor (100 μL) and vitreous humor (200 μL) were extracted for rapamycin analysis. Erythromycin was used as an internal standard (IS). Twenty five microliters of IS at a concentration of 5 μg/mL was added to all the tissue homogenate samples except blank and vortexed for 60 seconds. Rapamycin and the IS were extracted from the ocular tissue homogenates using protein precipitation method. Twenty five microliters of 50% triethyl amine in methanol (v/v) was added to all the samples and then vortexed vigorously for 2 min. Proteins were precipitated by adding to the above mixture with 800 μL of methanol and vortexed mixed for another 2 minutes. Samples were then centrifuged at 10,000 rpm for 30 min at 4° C. The supernatant, 500 μL, was then separated and evaporated using SpeedVac® (SAVANT Instruments, Inc., Holbrook, N.Y.). The dry residues were reconstituted in 100 μL of HPLC mobile phase (acetonitrile-water (80:20 v/v) with 0.1% formic acid) followed by vortexing for 2 min. Calibration curve standards for each individual tissue homogenates were prepared by spiking respective control tissues homogenates (blank) with varying concentrations (calibration curve range 10.48-1000 ng/mL) of rapamycin. Seven calibration curves (one per tissue) were prepared and analyzed along with each tissue homogenate sample analysis. One sample matrix per tissue was extracted from control treated eyes. All standards and samples were analyzed using LC-MS/MS.

Analytical Method for Rapamycin Analysis:

The analysis of rapamycin from the ocular tissue homogenates was performed using a triple quadrupole mass spectrometer with electrospray ionization (ESI) on a turbo ionspray source (API 3200; Applied Biosystems, Foster City, Calif., USA) coupled to a liquid chromatography system (Prominence HPLC shimadzu, Riverwood Drive, Columbia Md.-21046, USA) and reversed phase C8-column, 5 μm, 50×4.6 mm (Waters Corporation US) and column temperature was maintained at 40° C. (Flatron CH-30 column heater, flatiron systems Inc., USA). The mobile phase consisted of acetonitrile-water (80:20 v/v) with 0.1% formic acid and was pumped at a flow rate of 0.25 mL/min. The sample volume injected was 20 μL and the analysis run time was 7 min. Multiple reaction monitoring (MRM) mode was utilized to detect the compound of interest. MRM transition for rapamycin m/z[M+Na]+: 936.4/409.3 and for IS m/z[M+H]+: 734.4/576.5 were optimized. The calibration curve consisted of 10.48 ng/mL, 29.95 ng/mL, 187.20 ng/mL, 312.00 ng/mL, 480.00 ng/mL, 640.00 ng/mL, 800.00 ng/mL and 1000.00 ng/mL of rapamycin in respective tissue sample extracts. The lower limit of quantitation was determined to be 10.48 ng/mL.

Rapamycin levels in isolated ocular tissues is provided in Table 13. Units of ng/mL in the tissue extract was converted to ng/g tissue based on the actual weight of the tissue sample. Rapamycin was not detected in AH, VH and in the lens. The highest concentration was detected in cornea followed by iris-ciliary body, sclera and then retina/choroids (back of the eye tissue). It is noted that much higher than therapeutic levels of rapamycin with topical application is achieved in the retina/choroid (target for diabetic macular edema, retinal neovascularization, wet age related macular degeneration) when the formulation is applied topically. Micellar nanocarriers, due to their hydrophilic chains on the exterior may utilize the aqueous channels/pores of the sclera to permeate efficiently, the diameter of which ranges from 30 nm to 300 nm. In addition, the hydrophilic micellar corona helps evade the wash out of drugs into the systemic circulation by the conjunctival/choroidal blood vessels and lymphatics. Utilizing the sclera aqueous channels rapamycin traverses transscleral pathway and reaches the back of the eye (retina choroid). Here, the diffusion of drug into the aqueous humor, lens and vitreous humor is avoided due to hydrophobic nature of the drug. Therefore, side effects associated with repeated intravitreal injections can be avoided.

TABLE 13

| Ocular Tissue(s)/Fluids & Blood | C ± SD (ng/g) |
|---|---|
| Cornea | 2260.74 ± 507.11 |
| Iris ciliary muscles | 585.48 ± 80.06 |
| Sclera | 486.39 ± 89.99 |
| Choroid/Retina | 362.35 ± 56.17 |

For the preparation of mixed nanomicellar formulations of the present disclosure, two non-ionic surfactants, vitamin E TPGS and octoxynol-40, were selected which readily formed mixed nanomicelles. In an embodiment, 2.5% vitamin E TPGS and 2.0% octoxynol-40 was used for the fabrication of a voclosporin nanomicellar formulation of the present disclosure. In an embodiment, 4.5% vitamin E TPGS and 2.0% of octoxynol-40 was used for the fabrication of a rapamycin nanomicellar formulation of the present disclosure and a dexamethasone nanomicellar formulation of the present disclosure. Osmolality of the prepared formulations ranged from about 75 mOsm/kg to about 325 mOsm/kg. Mixed nanomicelles size, 0.2% rapamycin formulation, was determined with a particle size analyzer and was found to be 25.3±1.2 nm with a polydispersity index of 0.206. There was an increase in the size of rapamycin micelles when compared to voclosporin (~12 nm) and dexamethasone (~18 nm). Mixed nanomicelles dissociated and released the hydrophobic rapamycin to form a milky aqueous suspension at the temperature range of about 83° C. to about 90° C., with upon cooling, a regeneration time of approximately 2 min to approximately 3 min to form a clear solution again. Compared to a voclopsorin nanomicellar formulation, mixed nanomicellar formulations of dexamethasone and rapamycin dissociated at a much higher temperatures. Absorbance of the mixed nanomicelles was observed at 400 nm in a UV-Visible spectrophotometer using water as blank. The absorbance of the formulation was found to be negligible (0.033 AU). This shows that the formulation was clear and no drug precipitation was observed. Entrapment of rapamycin in a nanomicellar formulation was determined with UV-HPLC at a wavelength of 278 nm using C-8 column for separation. The column temperature was maintained at approximately 40° C. Entrapment efficiency of voclosporin or dexamethasone was determined with UV-HPLC at a wavelength of 210 nm and 254 nm respectively using Zorbax SB-phenyl column for separation. For voclosporin analysis the column temperature was maintained at 70° C.

The 0.2% mixed nanomicellar formulation containing rapamycin, administered topically, was used to study the level of rapamycin in various ocular tissues. The nanomicellar formulation showed therapeutic drug levels in retina/choroid (posterior segment of eye). No drug was detected in the vitreous humor. The drug levels were below limit of detection in the aqueous humor and lens. The highest concentration was detected in cornea followed by iris-ciliary body, sclera and then retina/choroid. Similar trend in drug delivery to the retina/choroid was observed with the calcineurin inhibitor (voclosporin), and corticosteroid (dexamethazone). Ocular tissue distribution data for voclosporin and dexamethasone showed approximately 252 ng/gm and approximately 50 ng/gm of tissue drug level respectively in the retina/choroid. Rapamycin formulation showed a tremendous increase in drug concentrations in retina and choroid. The concentration of drug detected in retina/choroid was approximately 370 ng/g of tissue (~1.5 fold and ~7.5 fold more than voclosporin and dexamethasone respectively). Table 14 below compares physical properties for a 0.2% voclosporin nanomicellar formulation of the present disclosure, a 0.1% dexamethasone nanomicellar formulation of the present disclosure and a 0.2% rapamycin nanomicellar formulation of the present disclosure.

TABLE 14

| Formulation | Particle size (nm) | Polydispersity index | Dissociation Temperature (° C.) | Regeneration time (min) | Absorbance |
|---|---|---|---|---|---|
| 0.2% Voclosporin | 12.5 | 0.156 | 55 | 3.3 | 0.026 |
| 0.1% Dexamethasone | 18.0 | 0.218 | N.D | N.D | 0.025 |
| 0.2% Rapamycin | 25.0 | 0.206 | 90 | 2.9 | 0.033 |

N.D—Not determined (above 100° C.)

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An aqueous ophthalmic solution comprising nanomicelles in a physiologically acceptable buffer, having a pH of 5.0 to 8.0, wherein the nanomicelles consist essentially of dexamethasone, vitamin E TPGS and octoxynol-40, wherein the dexamethasone at a concentration ranging from about 0.01% w/v to about 1.00% w/v is solubilized through entrapment in a mixed micellar hydrophobic core with a corona composed of hydrophilic chains extending from the hydrophobic core, wherein the vitamin E TPGS at a concentration ranging from about 2.0% w/v to about 5.0% w/v is stabilized with the octoxynol-40 at a concentration ranging from about 1.0% w/v to about 3.0% w/v, wherein the aqueous ophthalmic solution is stable after about 40 days at about 4° C.

2. The aqueous ophthalmic solution of claim 1 wherein the concentration of the dexamethasone is from about 0.05% w/v to about 0.25% w/v.

3. The aqueous ophthalmic solution of claim 1 wherein the pH is in a range from about 6.6 to about 7.0.

4. The aqueous ophthalmic solution of claim 1 wherein the concentration of the vitamin E TPGS is from about 4.0% w/v to about 5.0% w/v.

5. The aqueous ophthalmic solution of claim 1 wherein the concentration of the octoxynol-40 is from about 1.5% w/v to about 2.5% w/v.

6. An eye drop formulation comprising nanomicelles in a physiologically acceptable buffer, wherein the nanomicelles consist essentially of:
 dexamethasone at a concentration ranging from about 0.01% w/v to about 1.00% w/v;
 vitamin E TPGS at a concentration ranging from about 2.0% w/v to about 5.0% w/v; and
 octoxynol-40 at a concentration ranging from about 1.0% w/v to about 3.0% w/v, wherein the dexamethasone is solubilized through entrapment in a mixed micellar hydrophobic core of the vitamin E TPGS and the octoxynol-40, wherein the aqueous ophthalmic solution is stable after about 40 days at about 4° C.

7. The eye drop formulation of claim 6 wherein the concentration of the dexamethasone is from about 0.05% w/v to about 0.25% w/v.

8. The eye drop formulation of claim 6 wherein the concentration of the vitamin E TPGS is from about 4.0% w/v to about 5.0% w/v.

9. The eye drop formulation of claim 6 wherein the concentration of the octoxynol-40 is from about 1.5% w/v to about 2.5% w/v.

10. The eye drop formulation of claim 6 wherein the dexamethasone is present in the formulation at a concentration of about 0.1 wt % w/v, the vitamin E TPGS is present in the formulation at a concentration of about 4.5% w/v, and the octoxynol-40 is present in the formulation at a concentration of about 2.0% w/v.

11. A kit comprising:
 a unit dose of an aqueous ophthalmic solution comprising nanomicelles in a physiologically acceptable buffer, having a pH of 5.0 to 8.0, wherein the nanomicelles consist essentially of dexamethasone, vitamin E TPGS and octoxynol-40, wherein the dexamethasone at a concentration ranging from about 0.01% w/v to about 1.00% w/v is solubilized through entrapment in a mixed micellar hydrophobic core with a corona composed of hydrophilic chains extending from the hydrophobic core, wherein the vitamin E TPGS at a concentration ranging from about 2.0% w/v to about 5.0% w/v is stabilized with the octoxynol-40 at a concentration ranging from about 1.0% w/v to about 3.0% w/v, wherein the unit dose in contained within a vial prepared from a pharmaceutically acceptable packaging material, wherein the aqueous ophthalmic solution is stable after about 40 days at about 4° C.

12. The kit of claim 11 wherein the unit dose is about 50 μL.

13. The kit of claim 11 wherein the dexamethasone is present in the formulation at a concentration of about 0.1 wt % w/v, the vitamin E TPGS is present in the formulation at a concentration of about 4.5% w/v, and the octoxynol-40 is present in the formulation at a concentration of about 2.0% w/v.

14. The kit of claim 11 wherein the pharmaceutically acceptable packaging material is low density polyethylene or high density polyethylene.

15. A method of treating a back-of-the-eye ocular condition with dexamethasone in a patient in need thereof comprising:
 administering to an eye of a patient an effective amount of an aqueous ophthalmic solution comprising nanomicelles in a physiologically acceptable buffer, having a pH of 5.0 to 8.0, wherein the nanomicelles consist essentially of dexamethasone, vitamin E TPGS and octoxynol-40, wherein the dexamethasone at a concentration ranging from about 0.01% w/v to about 1.00% w/v is solubilized through entrapment in a mixed micellar hydrophobic core with a corona composed of hydrophilic chains extending from the hydrophobic core, wherein the vitamin E TPGS at a concentration ranging from about 2.0% w/v to about 5.0% w/v is stabilized with the octoxynol-40 at a concentration ranging from about 1.0% w/v to about 3.0% w/v, wherein the aqueous ophthalmic solution is stable after about 40 days at about 4° C.

16. The method of claim 15 wherein the dexamethasone is present in the solution at a concentration of about 0.1 wt % w/v, the vitamin E TPGS is present in the solution at a concentration of about 4.5% w/v, and the octoxynol-40 is present in the solution at a concentration of about 2.0% w/v.

* * * * *